United States Patent [19]

Narula et al.

[11] Patent Number: 5,346,884

[45] Date of Patent: Sep. 13, 1994

[54] SUBSTITUTED 2,6-DIMETHYLBICYCLO[3,3,1]NON-6-ENES, PROCESSES FOR PREPARING SAME AND ORGANOLEPTIC USES THEREOF

[75] Inventors: Anubhav P. S. Narula; Matthew J. McGinnis, both of Hazlet; Charles E. J. Beck, Summit; Marie R. Hanna, Keyport, all of N.J.; Franc T. Schiet, New York, N.Y.

[73] Assignee: International Flavors & Fragrances Inc., New York, N.Y.

[21] Appl. No.: 130,396

[22] Filed: Oct. 1, 1993

[51] Int. Cl.$^5$ .............................................. A61K 7/46
[52] U.S. Cl. ........................................ 512/6; 558/428; 512/17; 568/445
[58] Field of Search ...................... 512/6, 17; 558/428; 568/445

[56] References Cited

U.S. PATENT DOCUMENTS 4,956,481  9/1990  Gillaspey et al. ................... 549/459

Primary Examiner—James H. Reamer
Attorney, Agent, or Firm—Arthur L. Liberman

[57] ABSTRACT

Described are substituted 2,6-dimethylbicyclo[3,3,1]-non-6-enes defined according to the generic structure:

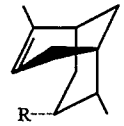

wherein the dashed line represents a carbon-carbon single bond or a carbon-carbon double bond and wherein "R" represents one of the moieties:

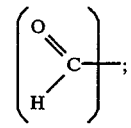

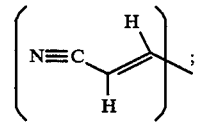

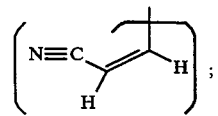

or

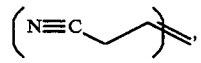

processes for preparing same and uses thereof in augmenting or enhancing the aroma of consumable materials including perfume compositions, colognes and perfumed articles (e.g., solid or liquid anionic, cationic, nonionic or zwitterionic detergents, hair preparations, fabric softeners, fabric softener articles, cosmetic powders and perfumed polymers).

21 Claims, 12 Drawing Sheets

GLC PROFILE FOR EXAMPLE I.

GLC PROFILE FOR EXAMPLE I.

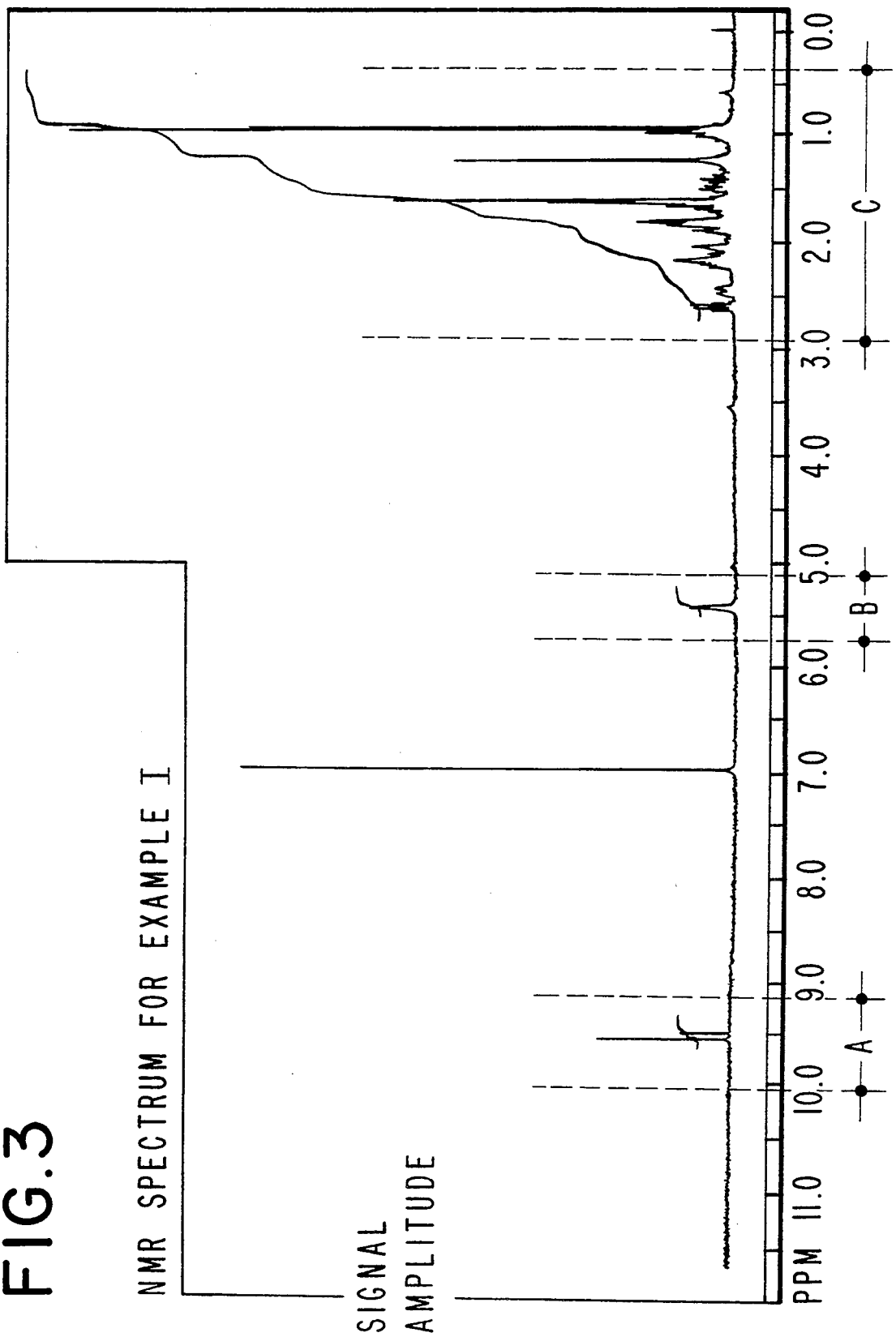

FIG. 3-A
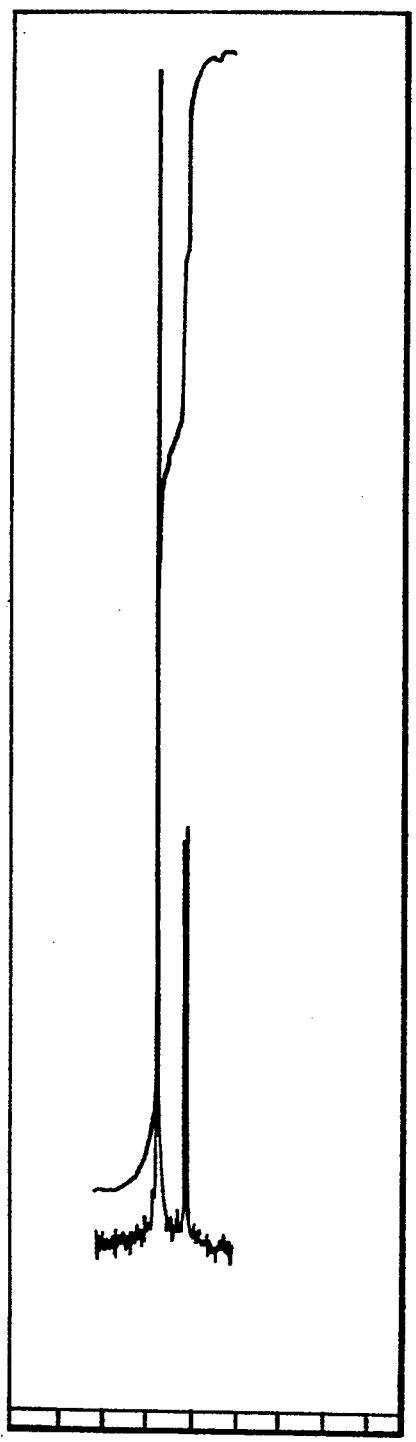
9.6
PPM
FIG. 3-B
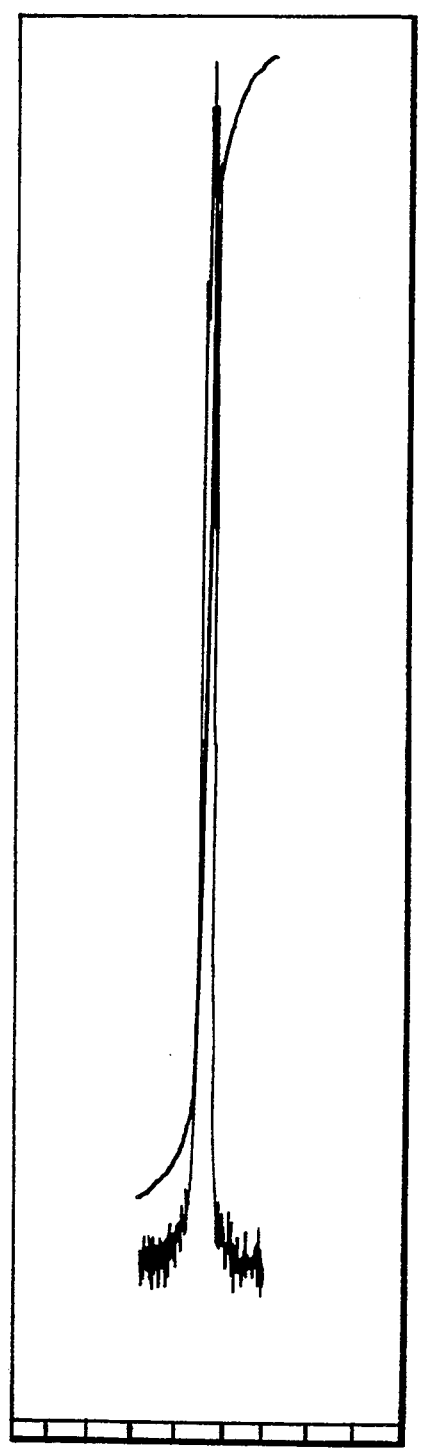
5.4
PPM

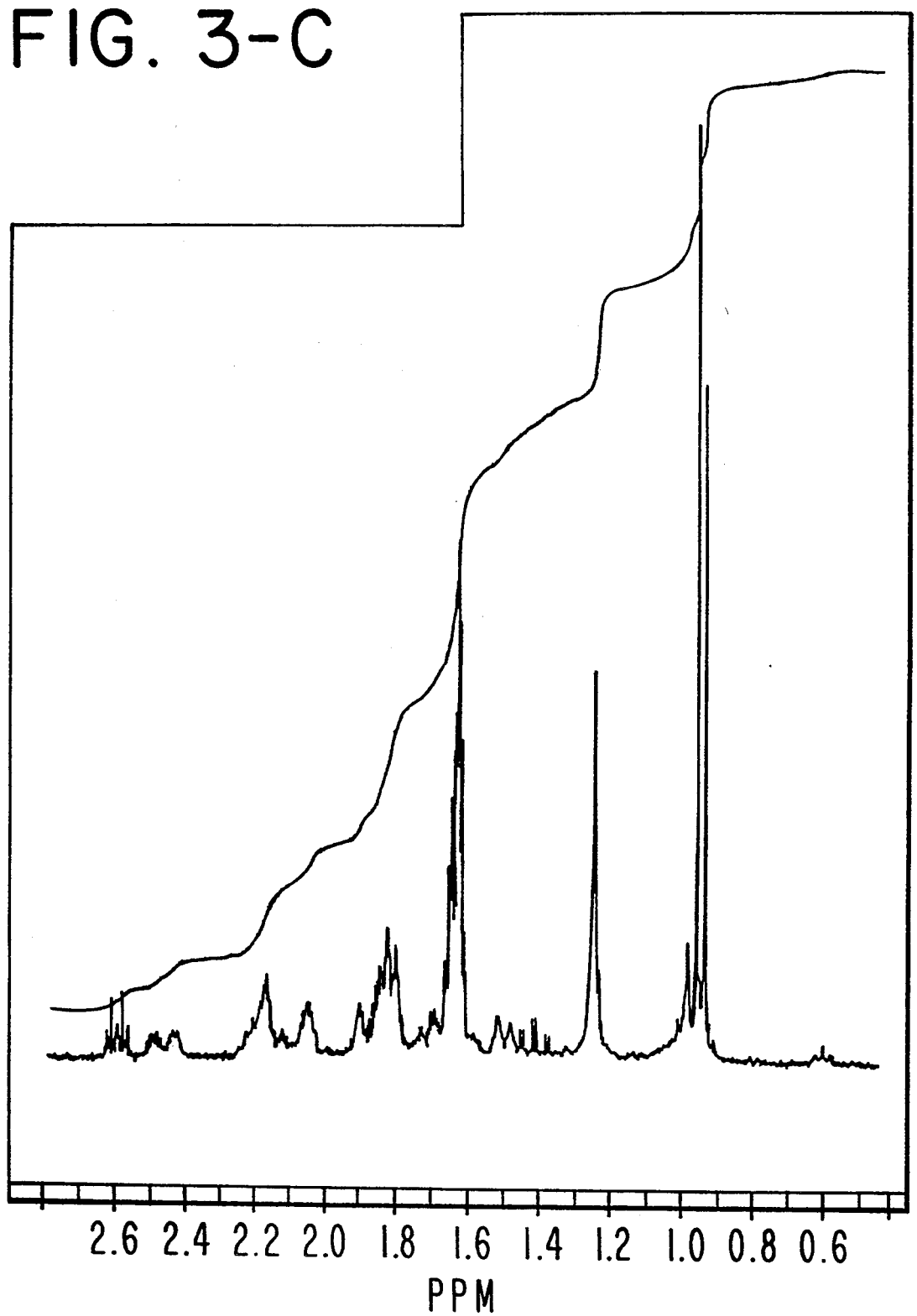
FIG. 3-C

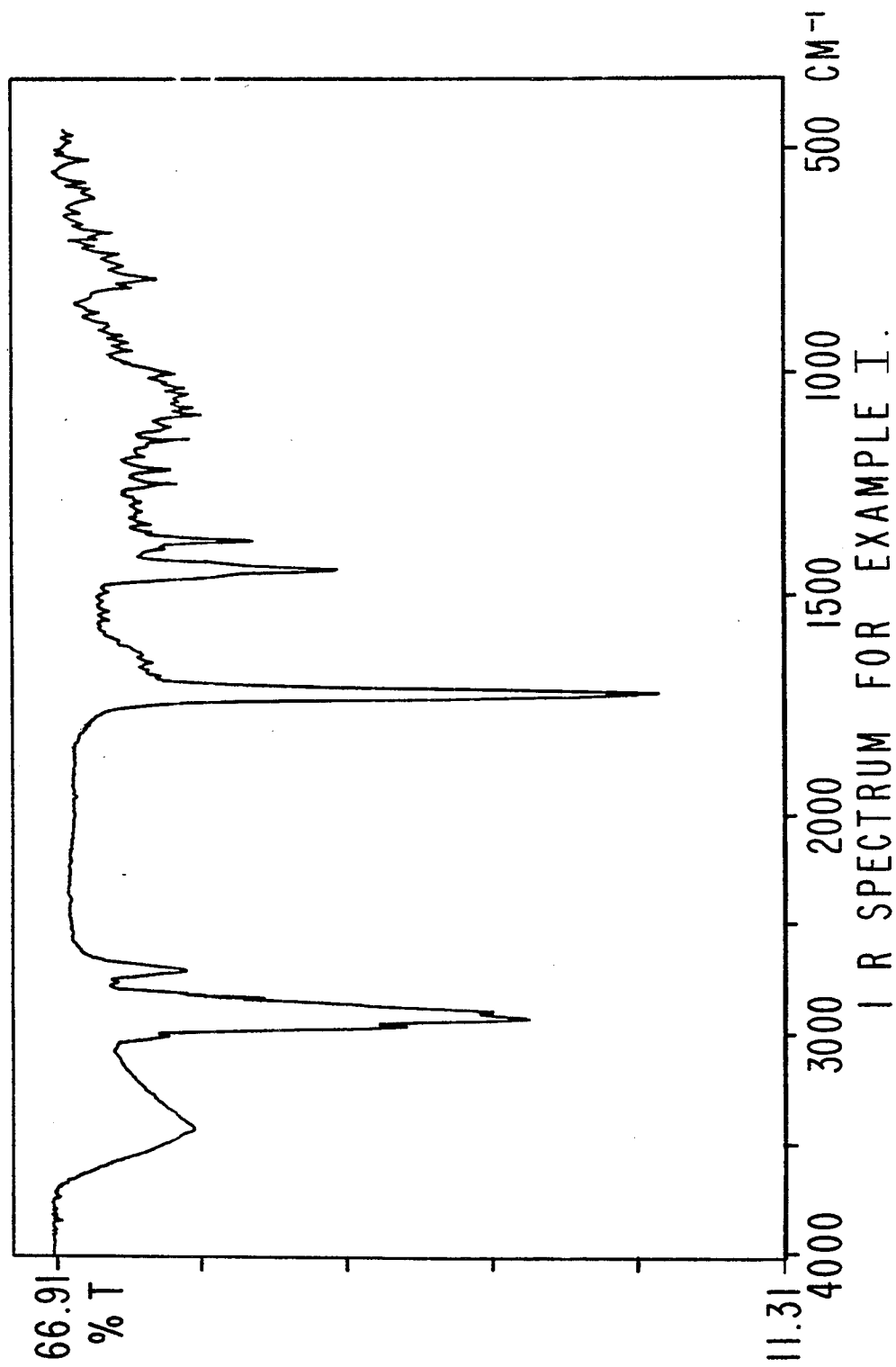

GLC PROFILE FOR EXAMPLE II.

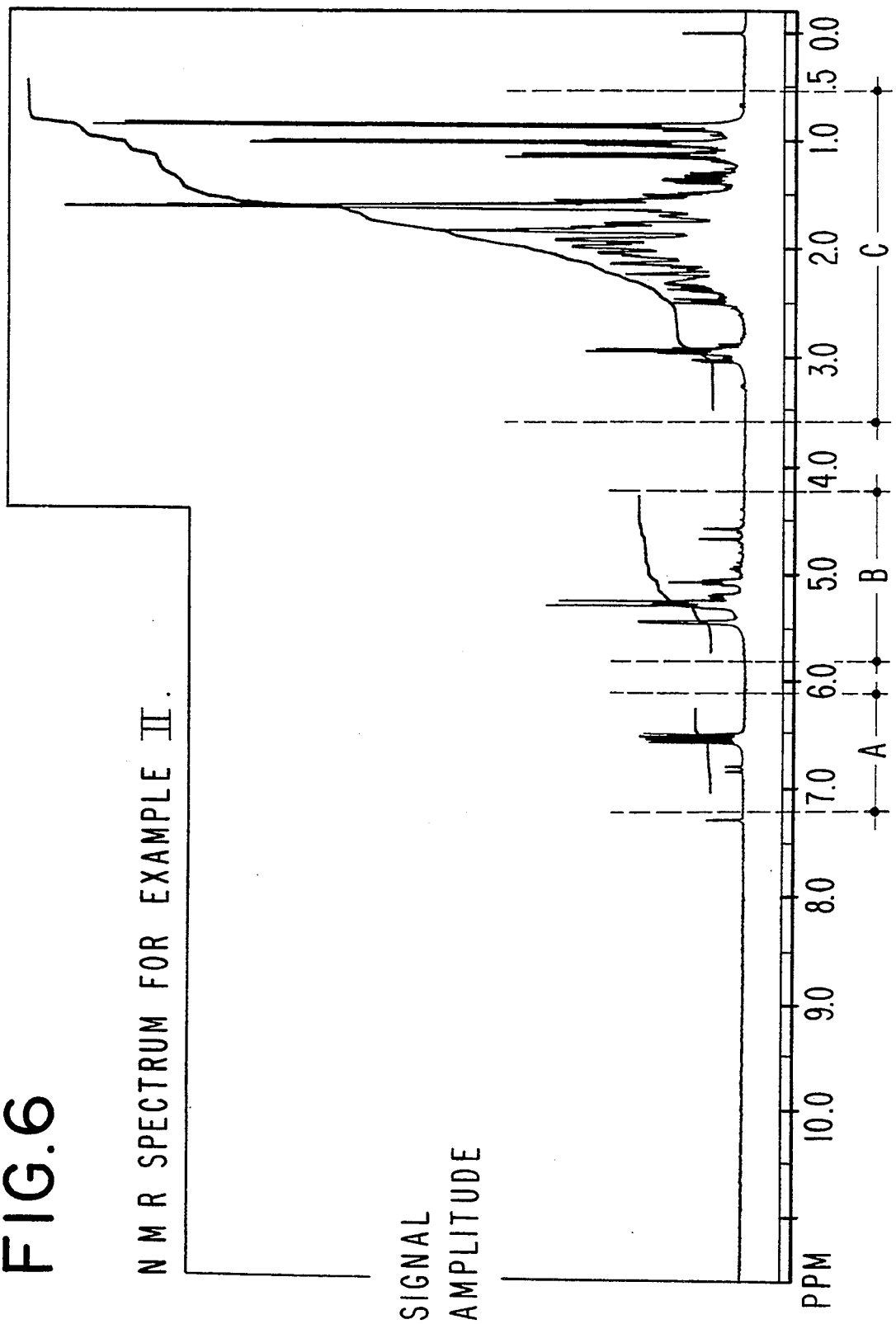
FIG.6 NMR SPECTRUM FOR EXAMPLE II.

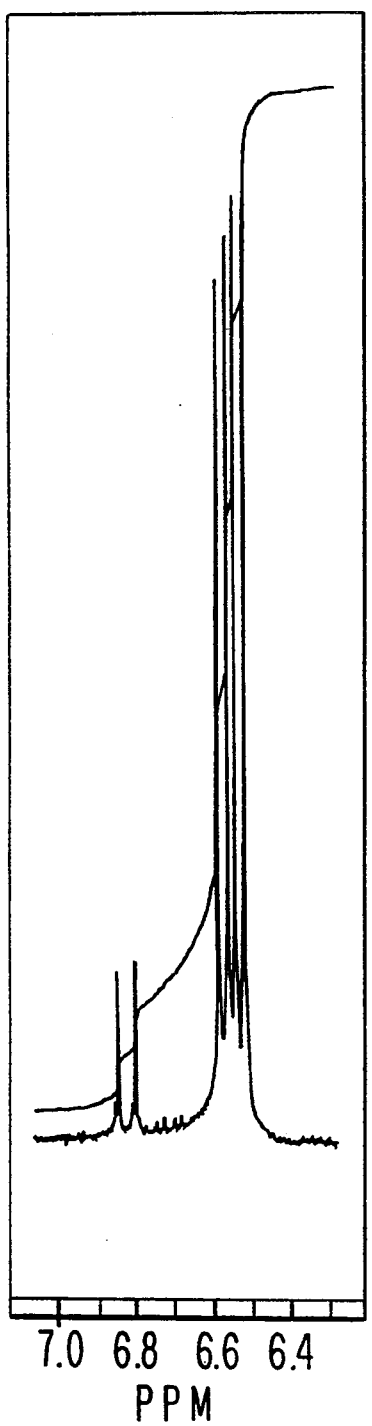
FIG.6-A
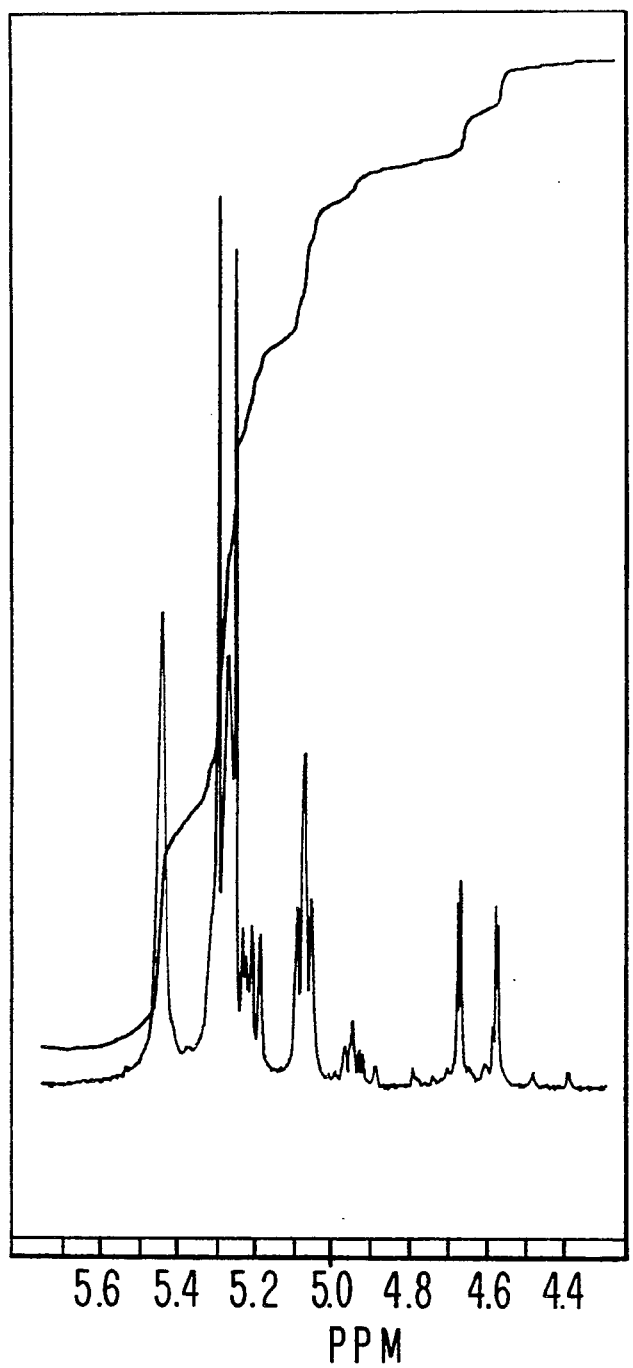
FIG.6-B

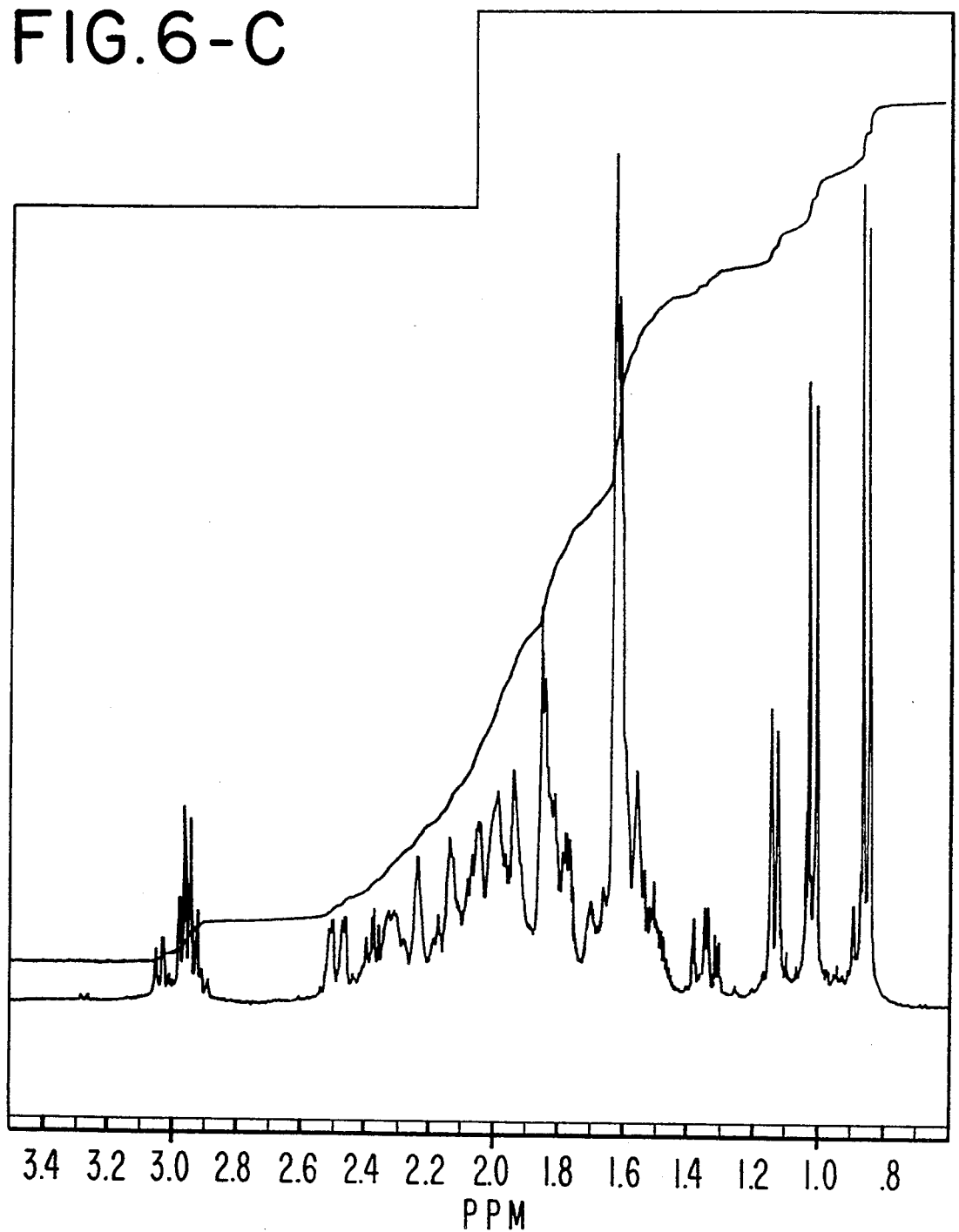
FIG.6-C

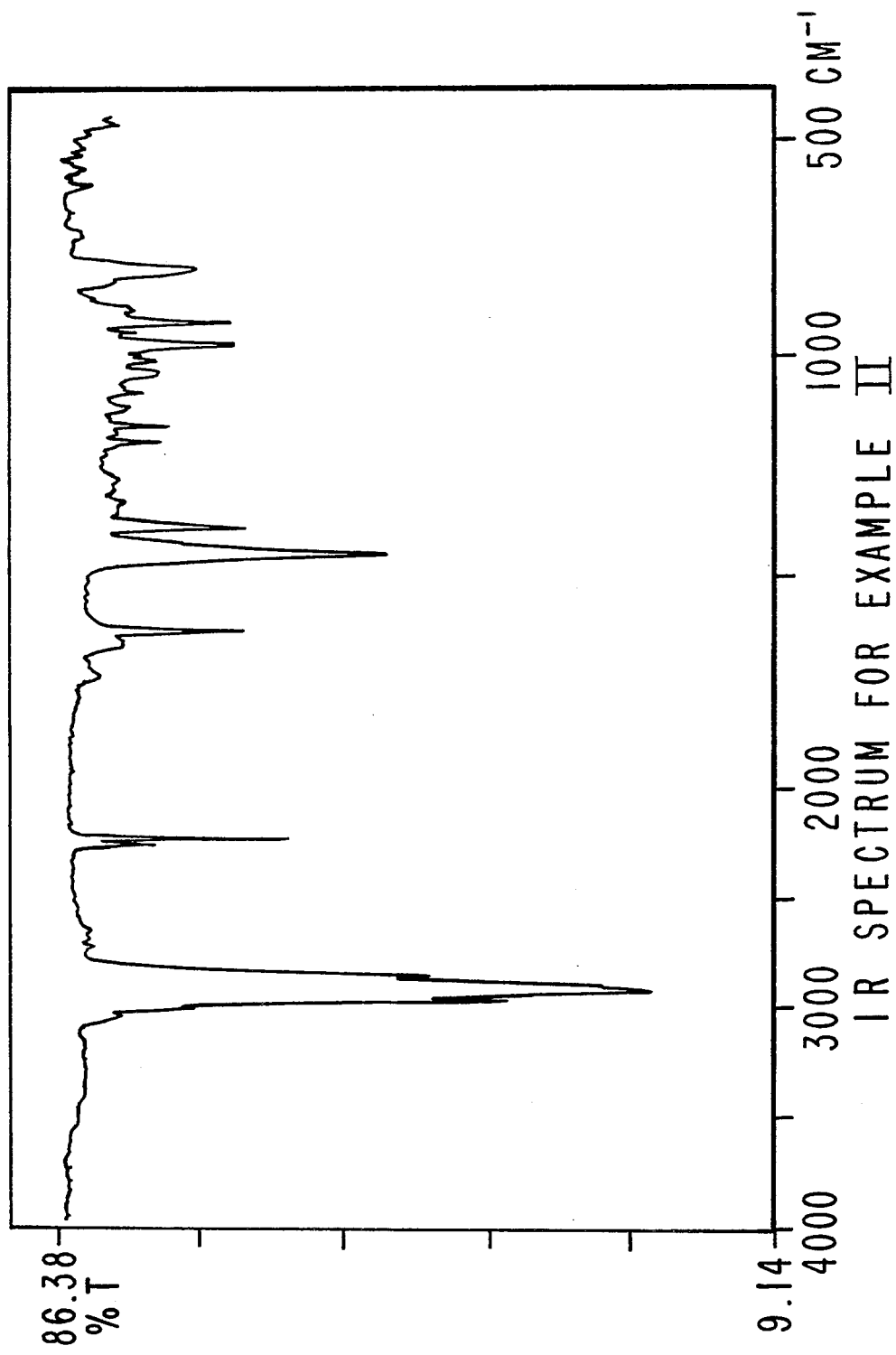
FIG. 7 IR SPECTRUM FOR EXAMPLE II

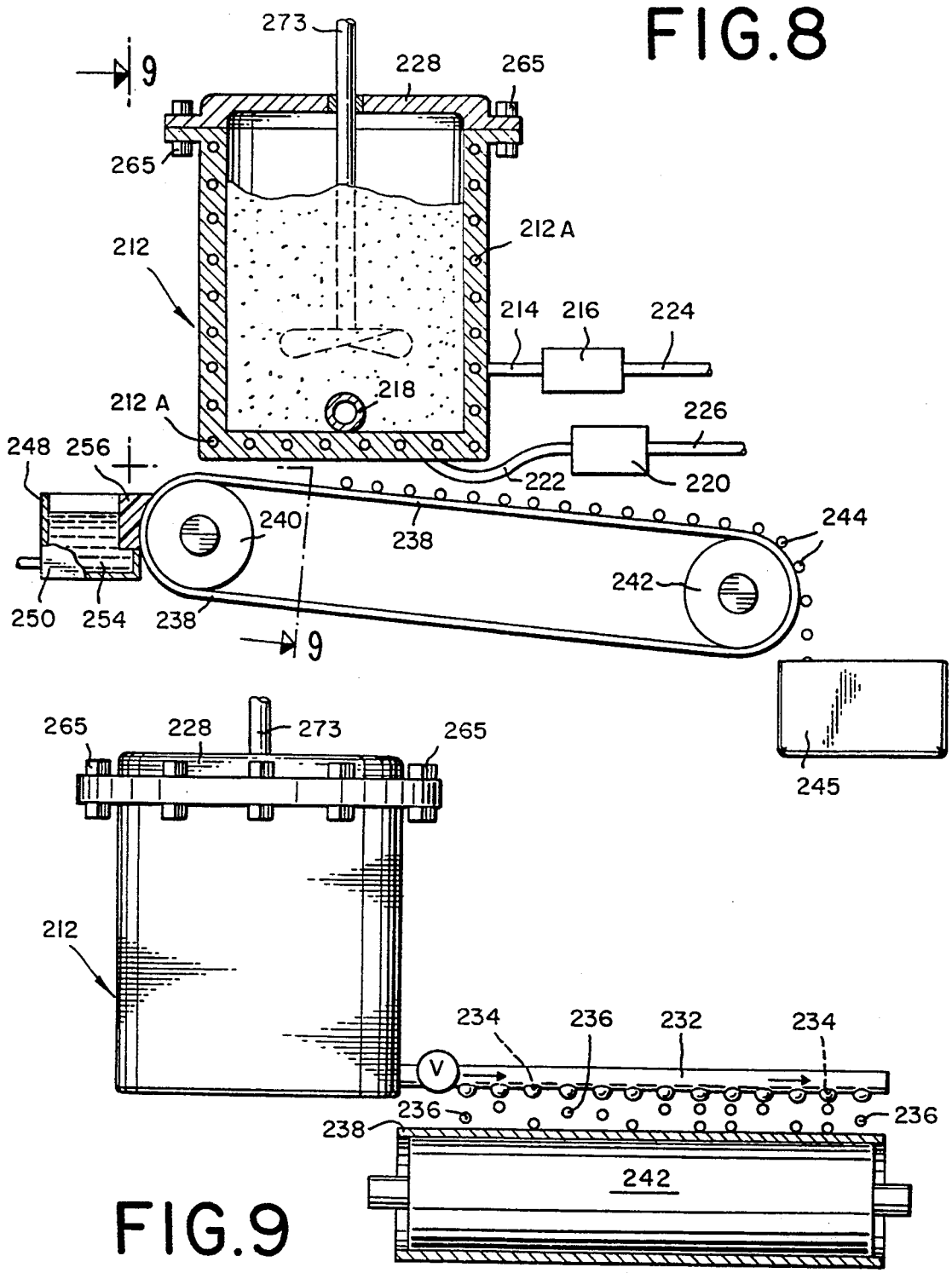

SUBSTITUTED 2,6-DIMETHYLBICYCLO[3,3,1]NON-6-ENES, PROCESSES FOR PREPARING SAME AND ORGANOLEPTIC USES THEREOF

BACKGROUND OF THE INVENTION

The instant invention relates to substituted 2,6-dimethylbicyclo[3,3,1]non-6-enes defined according to the generic structure:

wherein the dashed line represents a carbon-carbon single bond or a carbon-carbon double bond and wherein the moiety "R" represents one of the moieties:

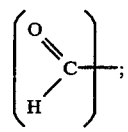

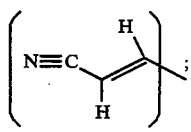

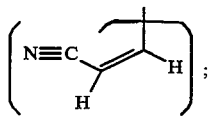

or

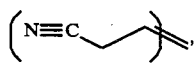

processes for preparing same and organoleptic uses of said substituted 2,6-dimethylbicyclo[3,3,1]non-6-enes in augmenting or enhancing the aroma of consumable materials.

There has been considerable work performed relating to substances which can be used to impart (modify, augment or enhance) fragrances to (or in) various consumable materials. These substances are used to diminish the use of natural materials some of which may be in short supply and to provide more uniform properties in the finished product.

Long-lasting, substantive and intense earthy, camphoraceous, woody, green, mimosa and violet leaf aroma nuances with rooty, vetiver, green, fruity, woody, violet leaf and mimosa topnotes are desirable in several types of perfume compositions, perfumed articles, colognes, deodorizing compositions and odor maskant materials.

The use of polycyclic nitrile and carboxaldehyde derivatives in perfumery for augmenting or enhancing the aromas of perfumed compositions, perfumed articles and colognes is well known in the art. Thus, the compound having the structure:

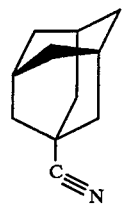

is indicated to have perfume utility in Chemical Abstracts Volume 71:94695w (abstract of Netherlands Published Patent Application 6715903, published on May 28, 1969). U.S. Pat. No. 4,956,481 issued on Sep. 11, 1990 (the specification for which is incorporated herein by reference) discloses the perfumery use of the compound having the structure:

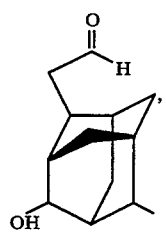

described as having a "green, woody and fir balsam-like aroma profile". Furthermore, U.S. Pat. No. 4,956,481 discloses the formation of the intermediate compound having the structure:

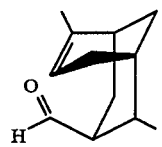

(along with many other compounds) in preparing the compound having the structure:

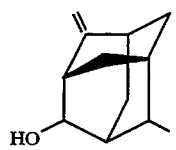

which is indicated therein as having "a camphoraceous, gingery cardamon and woody profile" or a "sandalwood, woody, patchouli, rhubarb, ginger, minty and amyris aroma profile with amyris, camphoraceous, patchouli, woody and piney topnotes".

U.S. Pat. No. 4,956,481 always shows the existence of the compound having the structure:

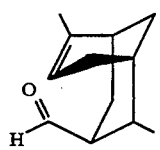

in small percentages in compositions along with the compound having the structure:

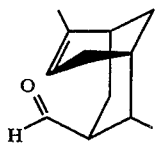

and either the compound having the structure:

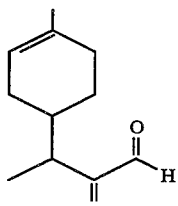

or the compound having the structure:

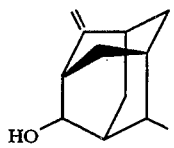

(which are in major proportion).

Thus, nothing in the prior art sets forth the existence of the compound having the structure:

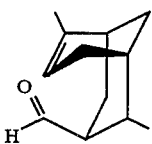

in substantially pure form or the compounds having the structures:

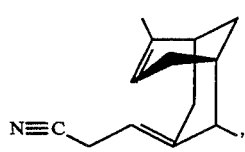

or the compounds having the structures:

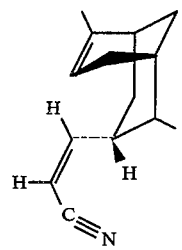

or

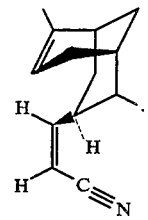

Furthermore, nothing in the prior art sets forth the existence of the intermediate compound having the structure:

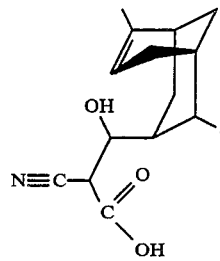

SUMMARY OF THE INVENTION

Our invention relates to substituted 2,6-dimethylbicyclo[3,3,1]non-6-enes defined according to the generic structure:

wherein the dashed line represents a carbon-carbon single bond or a carbon-carbon double bond and wherein R represents one of the moieties:

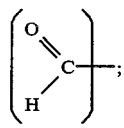

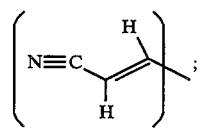

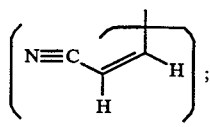

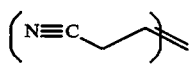

and processes for preparing same and uses thereof in augmenting, enhancing or imparting aromas in or to perfume compositions, perfumed articles and colognes. Our invention also relates to the process intermediate having the structure:

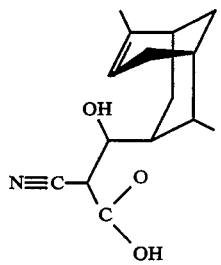

in all of its isomeric forms.

More specifically, our invention relates to the substantially pure compound having the structure:

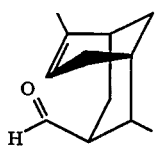

and its organoleptic uses in perfumery; the mixture of compounds defined according to the structure:

wherein in the mixture in each of the compounds one of the dashed lines represents a carbon-carbon double bond and the other of the dashed lines represents a carbon-carbon single bond; and the organic chemical process intermediate having the structure:

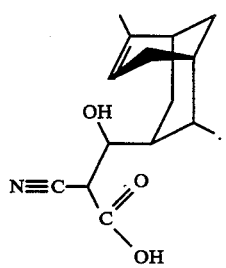

When referring to the structure, to wit:

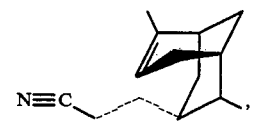

this structure represents a mixture of compounds which mixture includes the compounds having the structures:

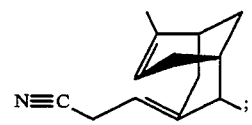

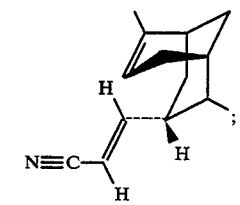

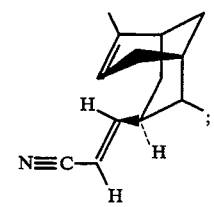

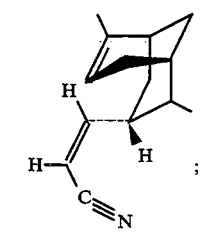

and

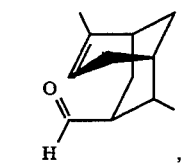

When referring to the compound having the structure:

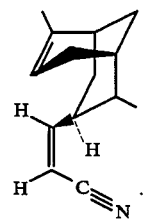

this structure too represents two different isomers, to wit:

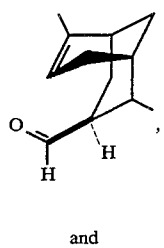

and

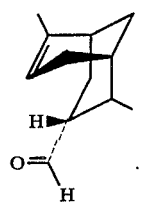

Indeed, the organic process intermediate having the structure:

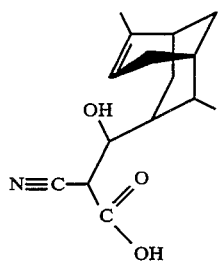

represents a mixture of optical isomers in view of the six asymmetric carbon atoms existing in the molecule.

Our invention also relates to processes for preparing the substituted 2,6-dimethylbicyclo[3,3,1]non-6-enes of our invention defined according to the generic structure:

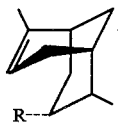

starting with the aldehyde having the structure:

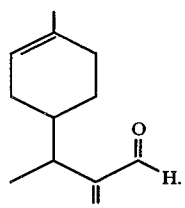

The aldehyde having the structure:

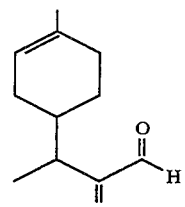

may be prepared according to the reaction:

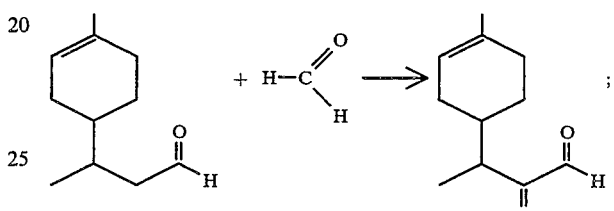

that is, according to Examples I or II of U.S. Pat. No. 4,956,481 issued on Sep. 11, 1990.

The aldehyde having the structure:

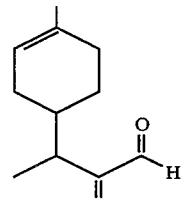

is then cyclized at a temperature of from about 180° C. up to about 220° C. according to the reaction:

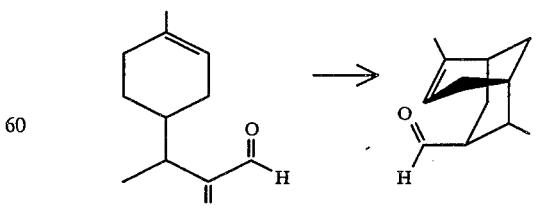

which takes place according to the reaction mechanism:

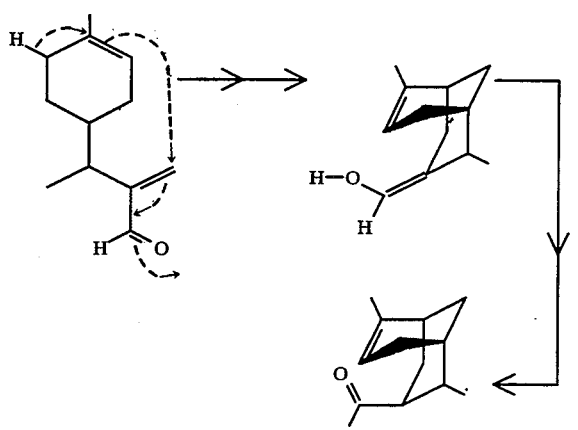

It is surprising that when using a temperature of from about 180° up to about 200° C. without the presence of any catalyst, the reaction ceases after the production of substantially pure compound having the structure:

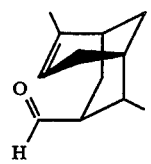

and does not proceed to the production of the compound having the structure:

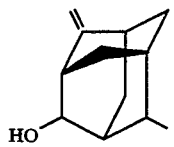

(as is taught in U.S. Pat. No. 4,956,481). Using temperatures of from about 200° up to about 220° C. the reaction will also cease with the production of substantially pure compound having the structure:

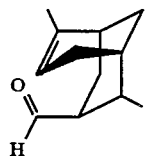

when using ALAMINE ® 336 catalyst. ALAMINE ® (ALAMINE ® 336 is a mixture of tri-$C_8$-$C_{10}$ alkyl amines manufactured by the Henkel Corporation (Extraction Technology Group) of Minneapolis, Minn. It is also known as ADOGEN ® 364 manufactured by the Ashland Company).

The resulting substantially pure aldehyde defined according to the structure:

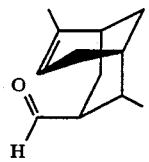

may then be used "as is" for its organoleptic properties or it may be further reacted with the compound having the structure:

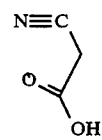

according to a Knoevenagel reaction, to wit:

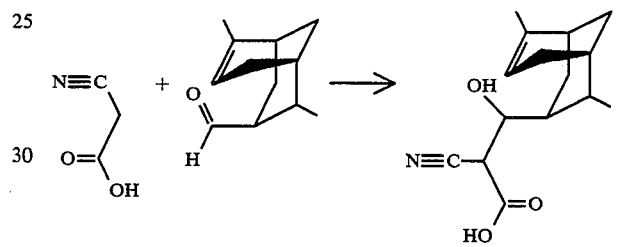

whereby the mixture of isomers defined according to the structure:

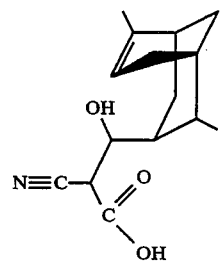

is prepared. This mixture of isomers may be isolated for use as a chemical intermediate or it may be further reacted by means of a dehydration reaction according to the reaction:

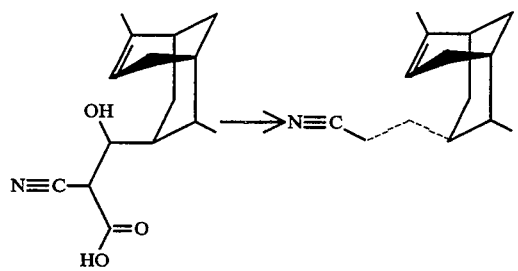

wherein, in the compound mixture defined:

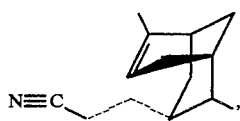

one of the dashed lines in the mixture of compounds represents a carbon-carbon double bond and the other of the dashed lines represent carbon-carbon single bonds and the mixture of compounds defined according to the structure:

contains the compounds having the structures:

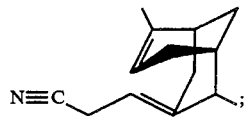

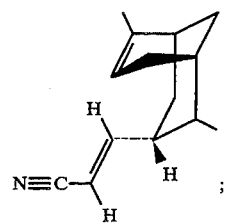

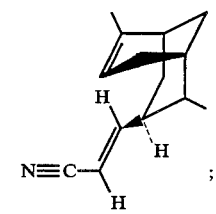

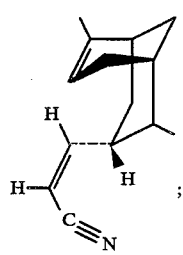

and

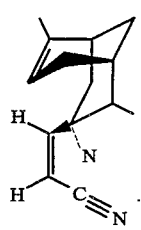

The mixture of compounds having the structure:

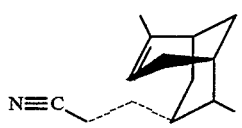

may then be "worked up" by appropriate reaction mass washing followed by fractional distillation.

Referring to the reaction:

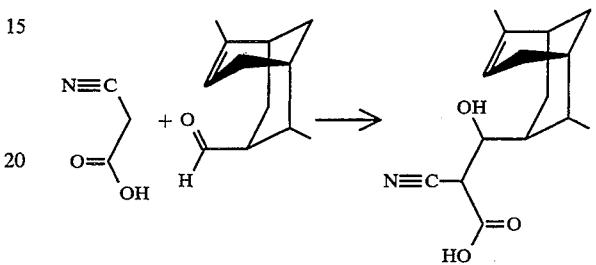

and the reaction:

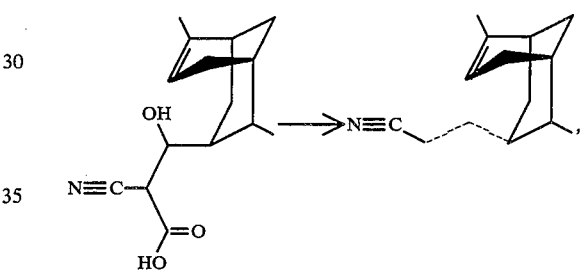

these reactions take place at a temperature in the range of from about 100° C. up to about 110° C. at reflux conditions at approximately atmospheric pressure in the presence of an appropriate inert solvent such as toluene. The reaction time may vary between about 5 hours and about 15 hours. Preferably present in the reaction mass (but not necessary) is ammonium acetate. The weight ratio of the compound having the structure:

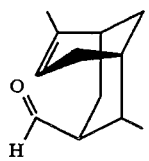

to the solvent, e.g., toluene is preferably about 1:1. The mole ratio of compound having the structure:

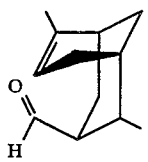

to compound having the structure:

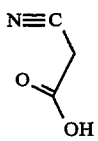

is from about 1:1 up to about 1:5 with a preferred mole ratio of about 1:1.25 (with the compound having the structure:

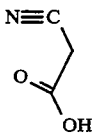

being preferred to be in molar excess). When it is used, the ammonium acetate:compound having the structure:

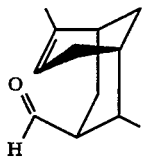

mole ratio is preferably about 0.3:1.

The substituted 2,6-dimethylbicyclo[3,3,1]non-6-enes of our invention have intense and substantive aromas which can be described as earthy, camphoraceous, woody, green, mimosa and violet leaf with rooty, vetivert, green, fruity, woody, violet leaf and mimosa topnotes. Table I below sets forth the summary of the particular compounds of our invention (or isomer mixtures thereof) and their aromas:

TABLE I

| Mixture of isomers defined according to the structure: 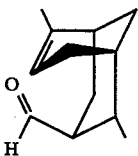 produced according to Example I distillation Fraction 4. | An earthy, comphoraceous aroma with rooty and vetivert topnotes. |
|---|---|
| Mixture of compounds defined according to the structure:  wherein in the mixture in each of the compounds one of the dashed lines represents a carbon-carbon double bond and the other of the dashed lines represents a carbon-carbon single bond produced | A woody, green, mimosa, violet-leaf aroma with green, fruity, woody, violet leaf and mimosa topnotes. |

TABLE I-continued according to Example II, bulked distillation Fractions 16–27.

The substituted 2,6-dimethylbicyclo[3,3,1]non-6-enes of our invention can be used to contribute earthy, camphoraceous, woody, green, mimosa and violet leaf aromas with rooty, vetivert, green, fruity, woody, violet leaf and mimosa topnotes to perfume compositions, perfumed articles, colognes, deodorizing articles, deodorizing compositions and malodor maskants. Examples of perfumed articles are anionic, cationic, nonionic and zwitterionic detergents, drier-added fabric softener compositions and drier-added fabric softener articles as well as hair preparations. As olfactory agents, the substituted 2,6-dimethylbicyclo[3,3,1]non-6-enes of our invention can be formulated into or used as components of a "perfume composition" or can be used as components of a "perfumed article" or the perfume composition may be added to perfumed articles.

The term "perfume composition" is used herein to mean a mixture of organic compounds including, for example, alcohols, aldehydes (other than the aldehydes of our invention); ketones, nitriles (other than the nitriles of our invention), ethers, lactones, natural essential oils, synthetic essential oils, and frequently hydrocarbons which are admixed so that the combined odors of the individual components produce a pleasant and desired fragrance. Such perfume compositions usually contain (a) the main note or the "bouquet" or foundation stone of the composition; (b) modifiers which round off and accompany the main note; (c) fixatives which include odorous substances which lend a particular note to the perfume throughout all stages of evaporation and substances which retard evaporation; and (d) topnotes which are usually low-boiling, fresh smelling materials.

In perfume compositions, the individual component will contribute its particular olfactory characteristics, but the olfactory effect of the perfume composition will be the sum of the effects of each of the perfume ingredients. Thus, the individual substituted 2,6-dimethylbicyclo[3 3 1]non-6-enes of our invention or mixtures thereof can be used to alter the aroma characteristics of a perfume composition, for example, by highlighting or moderating the olfactory reaction contributed by another ingredient in the composition.

The amount of the substituted 2,6-dimethylbicyclo[3,3,1]-non-6-ene(s) of this invention which will be effective in perfume compositions, depends on many factors including the other ingredients, their amounts, and the effects which are desired. It has been found that perfume compositions containing as little as 0.5% of one or more of the substituted 2,6-dimethylbicyclo[3,3,1]-non-6-enes of our invention or even less can be used to impart interesting intense and substantive earthy, camphoraceous, woody, green, mimosa and violet leaf aromas with rooty, vetivert, green, fruity, woody, violet leaf and mimosa topnotes to soaps, liquid and solid, anionic, cationic, nonionic and zwitterionic detergents, cosmetic powders, liquid and solid fabric softeners, optical brightener compositions, perfumed polymers and other products. The amount employed can range up to 50% or higher and will depend on considerations of cost, nature of the end product and the effect desired on the finished product and the particular fragrance sought.

The substituted 2,6-dimethylbicyclo[3,3,1]non-6-enes of this invention can be used alone or taken together with other perfumery components in perfume compositions as an olfactory component in detergents and soaps, space odorants and deodorants; colognes, toilet waters, bath salts, hair preparations, such as lacquers, brilliantines, pomades and shampoos; cosmetic preparations such as creams, deodorants, hand lotions and sun screens; powders such as talcs, dusting powders, face powders and the like. When used as an olfactory component of a perfumed article, as little as 0.01% of one or more of the substituted 2,6-dimethylbicyclo[3,3,1]non-6-enes of our invention will suffice to impart interesting, long-lasting, substantive earthy, camphoraceous, woody, green, mimosa and violet leaf aromas with rooty, vetivert, green, fruity, woody, violet leaf and mimosa topnotes. Generally, no more than 0.5% is required.

In addition, the perfume composition can contain a vehicle or carrier for the substituted 2,6-dimethylbicyclo[3,3,1]-non-6-enes taken alone or taken together with other ingredients. The vehicle can be a liquid such as an alcohol such as ethanol, a glycol such as propylene glycol or the like. The carrier can be an absorbent solid such as a gum, (e.g., gum arabic, guar gum and xanthan gum) or components for encapsulating the composition such as gelatin which can be used to form a capsule wall surrounding the perfume oil as by means of coacervation.

Our invention also relates to the utilization of controlled release technology for the controlled release of perfumes into gaseous environments; odor maskants and deodorizing agents into gaseous environments from polymers such as mixtures of epsilon polycaprolactone polymers and polyethylene which polyepsilon caprolactone polymers are described at Column 65 of U.S. Pat. No. 4,956,481 the specification for which is incorporated by reference herein.

Furthermore the method of incorporating the substituted 2,6-dimethylbicyclo[3,3,1]non-6-enes of our invention or perfume compositions containing same into polymers may be according to the technique of U.S. Pat. No. 3,505,432 issued on Apr. 7, 1970 (the specification for which is incorporated by reference herein) or U.S. Pat. No. 4,274,498 issued on Jan. 27, 1981, the disclosure of which is incorporated by reference herein.

Thus, for example, a first amount of liquid polyethylene-polyepsilon caprolactone polymer mixture (50:50) is mixed with one or more of the substituted 2,6-dimethylbicyclo[3,3,1]-non-6-enes of our invention. Drops are formed from the mixture and the drops are solidified. The solidified drops are then melted, if desired, with a second amount of unscented low density polyethylene, for example, or polypropylene, for example. Usually, but not necessarily, the second amount of polymer is larger than the first amount. The resulting mixture thus obtained is solidified subsequent to or prior to ultimate casting into a utilitarian shape.

Thus, in accordance with one aspect of our invention the imparting of scent is effected in two stages. In a first stage, a 50:50 (weight:weight) polyepsilon caprolactone, e.g., PCL ®-700 (trademark of Union Carbide Corporation):polyethylene in molten form is admixed with a high percentage of one or more of the substituted 2,6-dimethylbicyclo[3,3,1]-non-6-enes of our invention, e.g., the mixture of isomers having the structure:

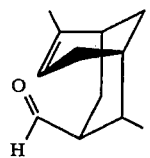

and the mixture is solidified in the form of pellets or beads. These pellets or beads thus contain a high percentage of substituted 2,6-dimethylbicyclo[3,3,1]non-6-enes (e.g., up to 45% by weight of the entire mixture) and may be used as "master pellets" which, thereafter, in a second stage, if desired, may be admixed and liquified with additional polymers such as additional polyethylene or mixtures of polyethylene and polyepsilon caprolactone in an unscented state, or unscented polypropylene. In addition, additional polymers or copolymers may be used, for example, copolymers specified and described in United Kingdom Patent Specification No. 1,589,201 published on May 7, 1981.

In accordance with the present invention at least one of the substituted 2,6-dimethylbicyclo[3,3,1]non-6-enes of our invention is added to the polymer in a large closed container or drum which is maintained under controlled temperature conditions while the polymer in a melted condition is mixed with at least one of the substituted 2,6-dimethylbicyclo[3,3,1]-non-6-enes of our invention under agitation.

In order that the perfume be added uniformly to the polymer, the temperature of the melt is constantly controlled during the process. The polymer-perfume mixture is then directed through an elongated conduit or pipe element having a plurality of orifices adjacent to the lower most portion thereof. The polymer enriched by at least one of the substituted 2,6-dimethylbicyclo[3,3,1]non-6-enes of our invention is permitted to drip through the orifices onto a continuously moving, cooled conveyor upon which the polymer containing at least one of the substituted 2,6-dimethylbicyclo[3,3,1]-non-6-enes of our invention solidifies into small size pellets with the perfume imprisoned therein. The apparatus useful in conjunction with this process advantageously includes a conveyor of a material which will not adhere to the polymer which contains at least one of the substituted 2,6-dimethylbicyclo[3,3,1]non-6-enes of our invention.

In order that the droplets form into uniform pellets or beads, the conveyor is continuously washed with a liquid such as water to maintain the surface relatively cool. The pellets are delivered by the conveyor into a container and packaged for shipment or for further incorporation into articles of manufacture, e.g., garbage bags (using the deodorization quality of the substituted 2,6-dimethylbicyclo[3,3,1]non-6-enes of our invention).

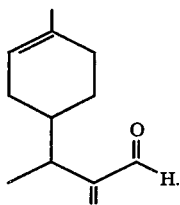

Figure 2:
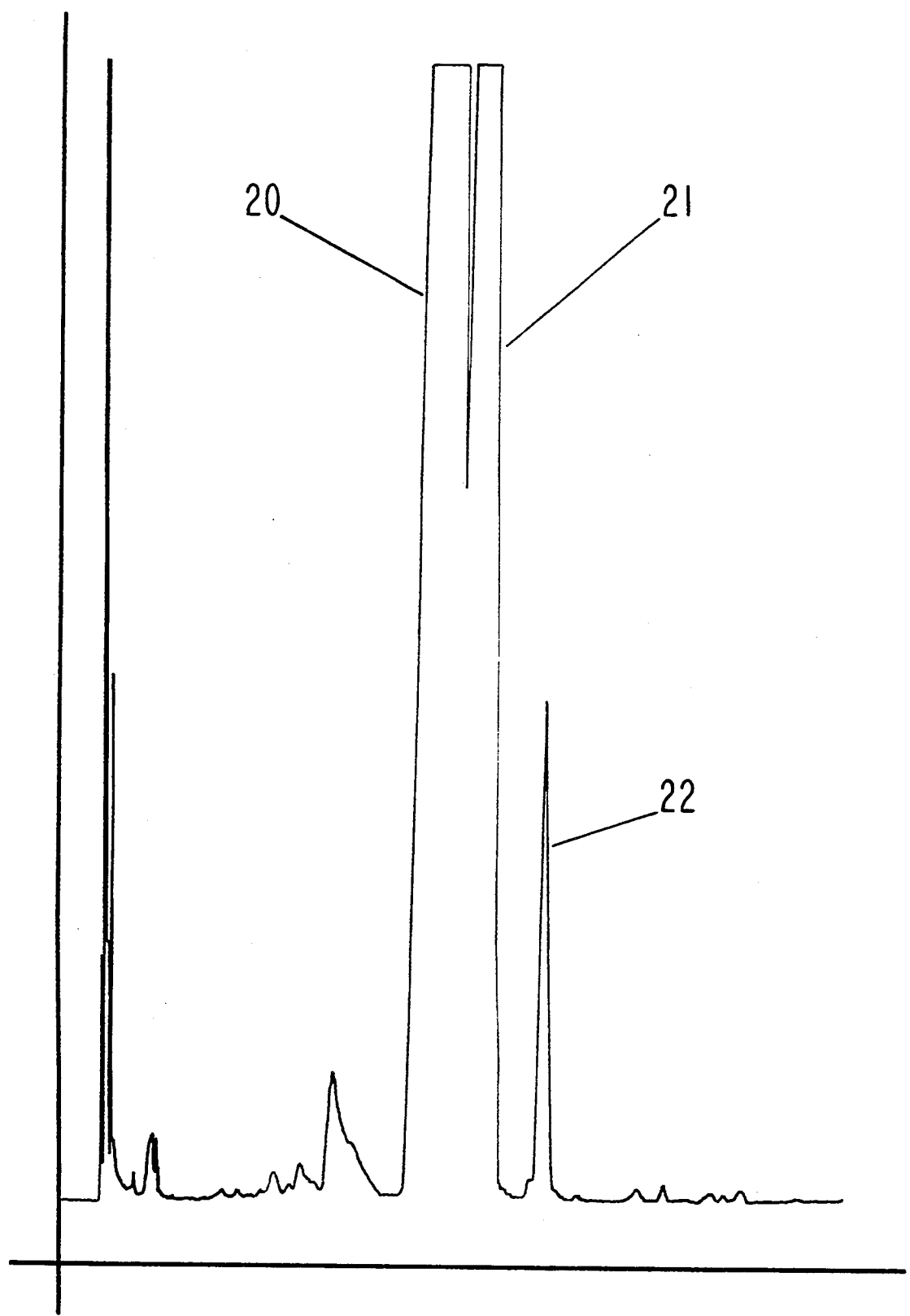

FIG. 2 is the GLC profile for the reaction product of Example I which contains a mixture of isomers having the structures:

and

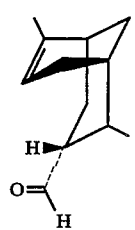

also indicated by the structure:

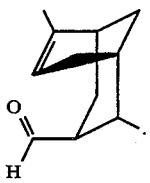

FIG. 3 is the NMR spectrum for the mixture of isomers indicated by the structure:

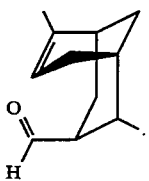

FIGS. 3A, 3B and 3C are enlargements of sections "A", "B" and "C" of the NMR spectrum of FIG. 3.

FIG. 4 is the infrared spectrum for the mixture of isomers produced according to Example I indicated by the structure:

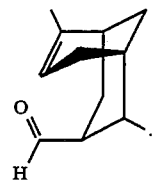

Figure 5:
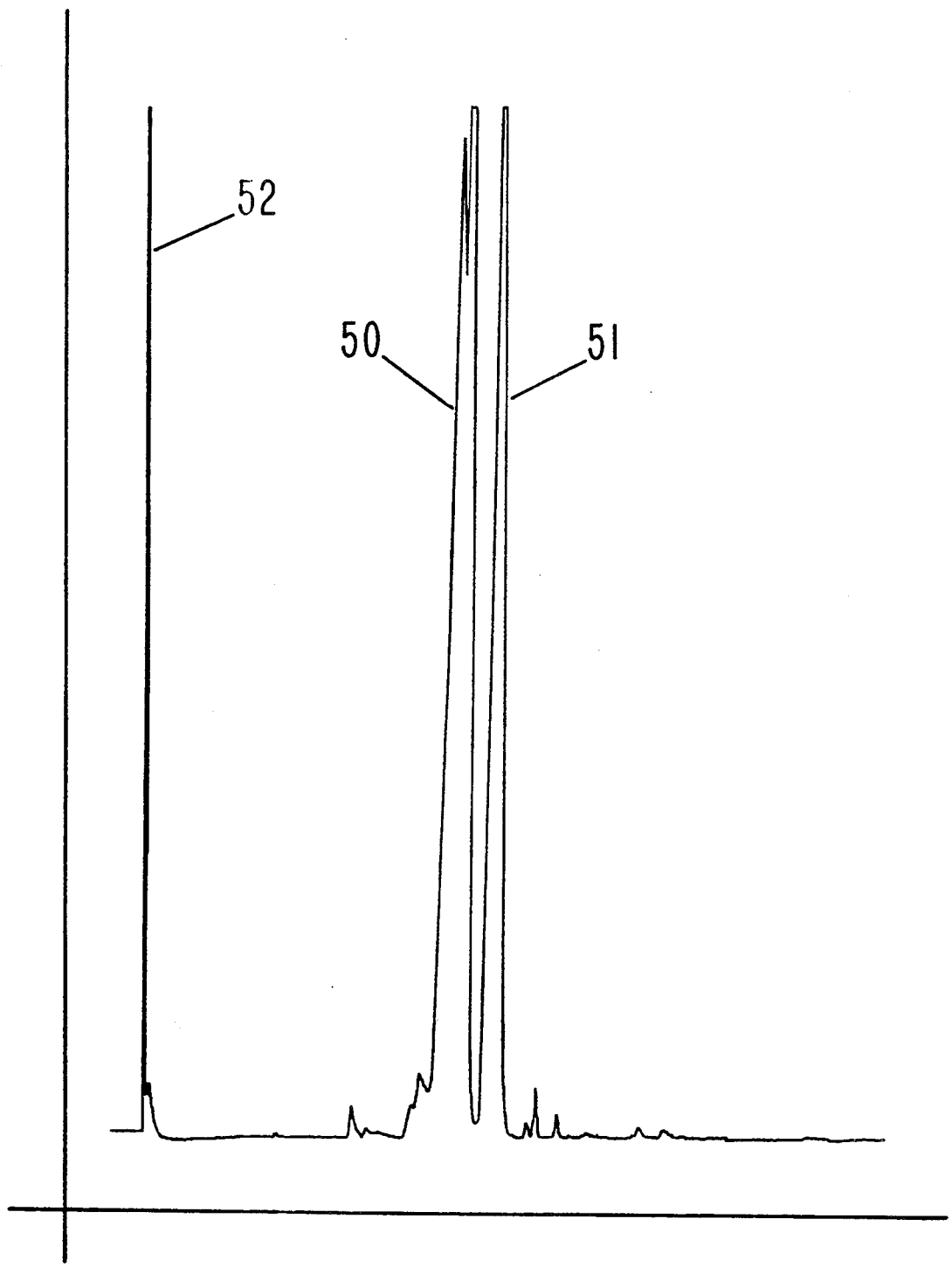

FIG. 5 is the GLC profile for the reaction product of Example II containing the compounds defined according to the structure:

wherein, in the mixture in each of the compounds one of the dashed lines represents a carbon-carbon single bond and the other of the dashed lines represents a carbon-carbon double bond.

FIG. 6 is the NMR spectrum of the mixture of compounds defined according to the structure:

prepared according to Example II.

FIGS. 6A, 6B and 6C are enlargements of sections "A", "B" and "C" respectively, of the NMR spectrum of FIG. 6.

FIG. 7 is the infrared spectrum for the mixture of compounds defined according to the structure:

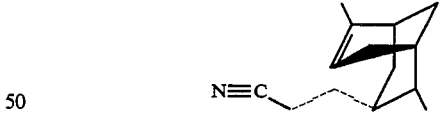

wherein, in the mixture in each of the compounds one of the dashed lines represents a carbon-carbon single bond and the other of the dashed lines represents a carbon-carbon double bond, produced according to Example II.

FIG. 8 is a partial side elevation and partial sectional view of an apparatus for forming polymer pellets containing at least one of the substituted 2,6-dimethylbicyclo-[3,3,1]-non-6-enes of our invention.

FIG. 9 is a section taken along line 9—9 of FIG. 8.

DETAILED DESCRIPTION OF THE DRAWINGS

Figure 1:
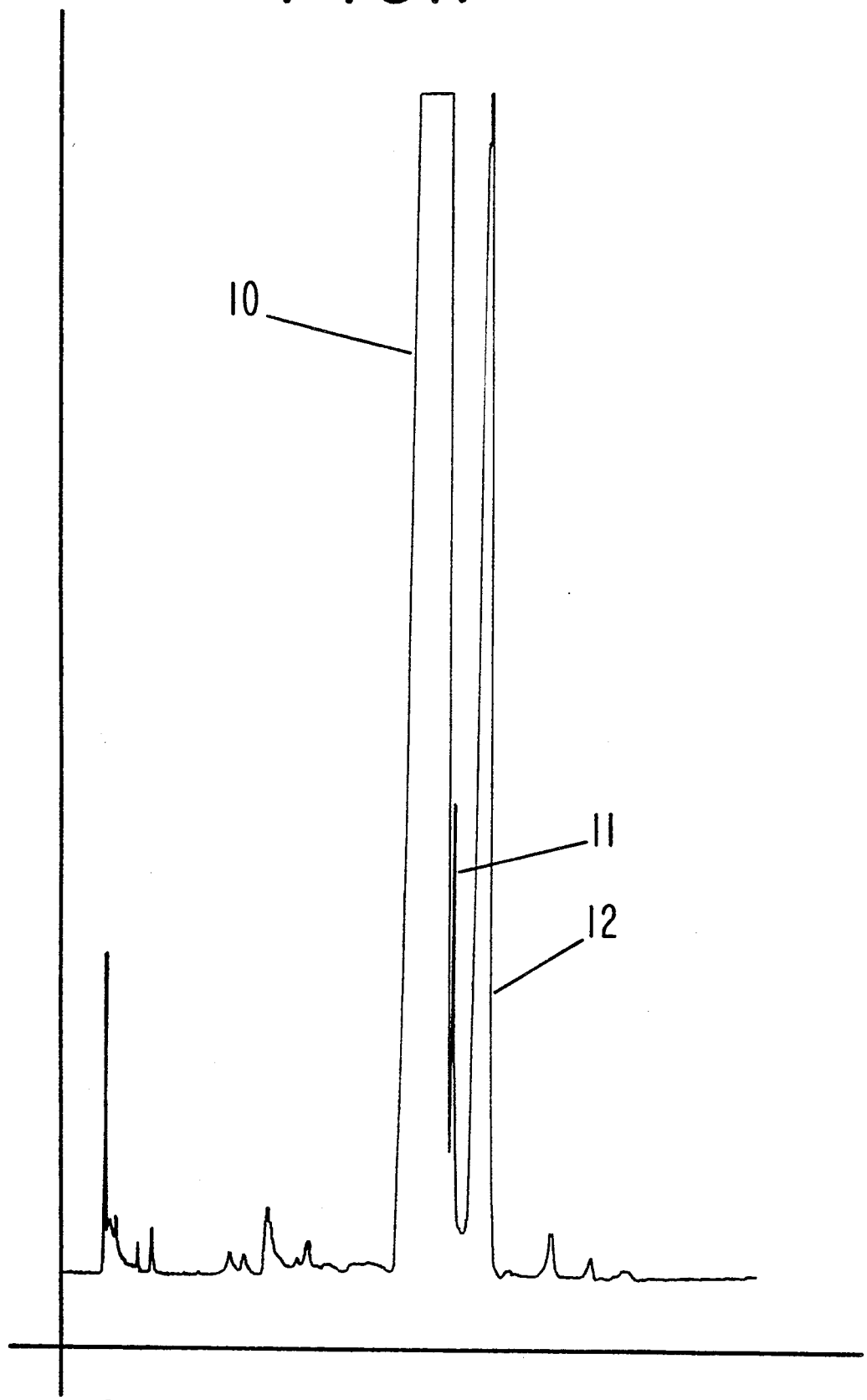
FIG. 1 is the GLC profile for the starting material for the reaction of Example I, which starting material is defined according to the structure.

FIG. 1 is the GLC profile for the starting material for the reaction:

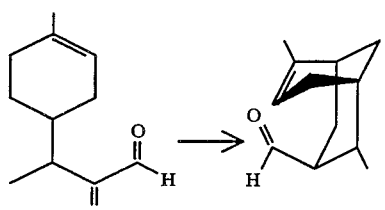

which starting material has the structure:

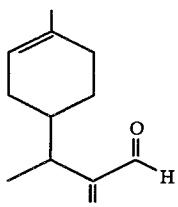

(Conditions: Carbowax column programmed at 130°–220° C. at 8° C. per minute) The peaks indicated by reference numerals 10, 11 and 12 are for isomers of the compound having the structure:

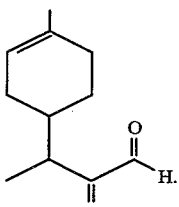

FIG. 2 is the GLC profile for the reaction product of Example I containing isomers of the compound having the structure:

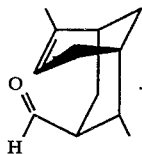

The peaks indicated by reference numerals 20 and 21 are for isomers of the compound having the structure:

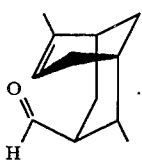

The peak indicated by reference numeral 22 is the peak for the compound having the structure:

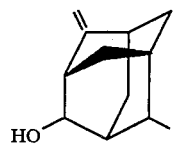

(which is removed from the reaction mass by distillation) prior to use thereof for subsequent reaction or for use thereof for its organoleptic properties.

FIG. 5 is the GLC profile for the reaction product of Example II containing a mixture of isomers defined according to the structure:

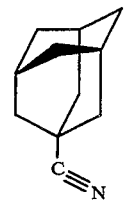

including the isomers having the structures:

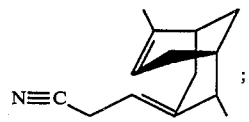;

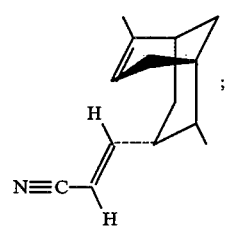;

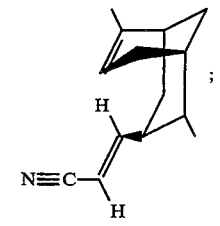;

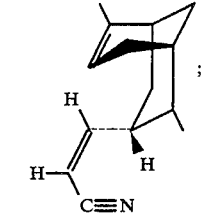;

and

-continued

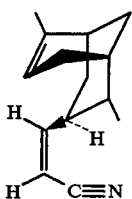

(Conditions: Carbowax column programmed at 130°–220° C. at 8° C. per minute). The peaks indicated by reference numerals 50 and 51 are for isomers having the structures:

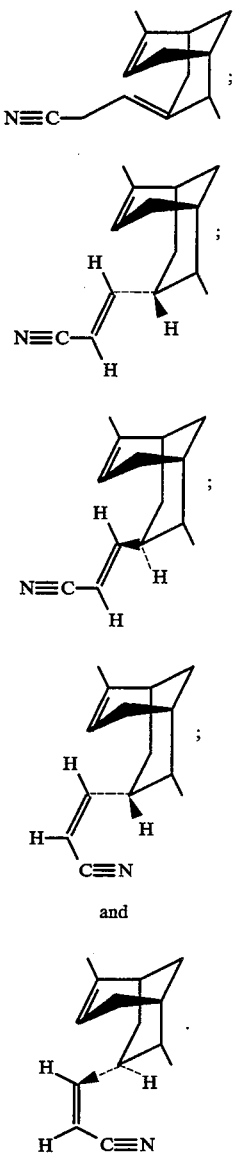

and

The peak indicated by reference numeral 52 is for the reaction solvent, toluene which is removed during the distillation step prior to uses of the nitriles for their organoleptic properties.

Referring to FIGS. 8 and 9, in particular, the apparatus used in producing polymeric fragrances containing one or more of the substituted 2,6-dimethylbicyclo[3,3,1]non-6-enes of our invention comprises a device for forming scented polyolefin (for example) pellets, which comprises a vat or container 212 into which a mixture of polyolefins such as polyethylene and an aromatic substance or scented material is placed (in this case at least one of the substituted 2,6-dimethylbicyclo[3,3,1]-non-6-enes of our invention). The container is closed by an airtight lid 228 and clamped to the container by bolts 265. A stirrer 273 traverses the lid or cover 228 in airtight manner and is rotated in a suitable manner. A surrounding cylinder 212 having heating coils 212A which are supplied with electric current through cable 224 from a rheostat or control 216 is operated to maintain a temperature inside the container 212 such that polyethylene or other thermoplastic polymer in the container will be maintained in the molten or liquid state. It has been found advantageous to employ a colorless odorless polymer (e.g., polyethylene) with viscosity ranging between 180 and 220 saybolt seconds and having a melting point in the range of 200°–280° F. The heating coils 212A is operated to maintain the upper portion of the container 212 within a temperature range of from 250°–350° F. The bottom portion of the container is heated by means of heating coils 212A heated through a control 220 connected thereto through a connecting wire 222 to maintain the lower portion of the container within a temperature range of from 250°–350° F.

Thus, polymer (e.g., polyethylene) is added to container 212 and is heated from 10–12 hours whereafter a scented aroma imparting material (at least one of the substituted 2,6-dimethylbicyclo[3,3,1]non-6-enes of our invention) is added quickly to the melt. The material must be compatible with the polyolefin and forms a homogeneous liquid melt therewith. The scented material is of a type for the particular aroma desired and formulated specifically for the scenting purpose for which the polyolefin will be employed.

Generally about 5–30% by weight of the scented material (containing at least one of the substituted 2,6-dimethylbicyclo[3,3,1]non-6-enes of our invention) are added to the polyolefin.

After the scent imparting material (e.g., a composition containing one of the substituted 2,6-dimethylbicyclo[3,3,1]-non-6-enes of our invention) is added to the container 212, the mixture is stirred for a few minutes, for example, 5–15 minutes and maintained within the temperature range as indicated previously by heating coils 212A. The controls 216 and 220 are connected, respectively, through cables 214 and 222, respectively, to heating coils 212A. The said controls 216 and 220 are also connected through cables 224 and 226, respectively, to a suitable power supply of electric current for supplying the electric power to the heating coils 212A for heating purposes.

Thereafter the valve "V" is opened permitting the mass to flow outwardly through conduit 218/232 having a multiplicity of orifices 234 adjacent to the lower side thereof. The outer end of the conduit 218/232 is closed so that the liquid polymer (e.g., polyolefin) and aroma imparting material (e.g., at least one of the substituted 2,6-dimethylbicyclo[3,3,1]non-6-enes of our invention) will continuously drop through orifices 234 downwardly from conduit 232. During this time the temperature of the polymer (e.g., polyethylene or polyolefin) and scent imparting material (e.g., at least one of the substituted 2,6-dimethylbicyclo[3,3,1]non-6-enes of our invention) is accurately controlled so that a temperature in the range of from about 210°-275° F. will exist in the conduit 218/232. The regulation of the temperature through the controls 216 and 220 is essential in order to insure temperature balance to provide for the continuous dropping or dripping of molten polymer (e.g., polyethylene) and scenting material (e.g., one or more of the substituted 2,6-dimethylbicyclo[3,3,1]non-6-enes of our invention) mixture through the orifices 234 at a rate which will insure the formation of droplets 236 which will fall downwardly onto a moving conveyor belt 238 caused to run between conveyor wheels 240 and 242 beneath the conduit 232.

When the droplets 236 fall onto the conveyor 238 they form pellets 244 which harden almost instantaneously and fall off the end of the conveyor 238 into a container 245 and utilized in processes as illustrated, infra.

A feature of this aspect of the process of our invention is the provision for moistening of the conveyor belt 238 to insure rapid formation of the solid polymeric (e.g., polyolefin) scented pellets 244 without sticking to material which will not normally stick to a melted plastic. A moistening means 248 insures a sufficiently cold temperature of the belt surface for adequate formation of the pellets 244. The adequate moistening means comprises a container 250 which is continuously fed with water 254 to maintain a level for moistening a sponge element 256 which bears against the exterior of the belt 238.

The following Examples I and II set forth preparation of the substituted 2,6-dimethylbicyclo[3,3,1]non-6-enes of our invention. Examples III, et seq. set forth the organoleptic uses of the substituted 2,6-dimethylbicyclo[3,3,1]non-6-enes of our invention prepared according to Examples I and II.

The following Examples I, et seq. serve to illustrate our invention and this invention is to be considered to be restricted thereto only as indicated in the appended claims.

All parts and percentages given herein are by weight unless otherwise specified.

EXAMPLE I

PREPARATION OF 2,6-DIMETHYLBICYCLO[3,3,]NON-6-ENYL CARBOXALDEHYDE

Reaction:

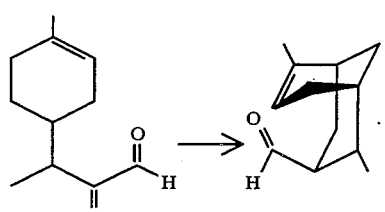

Into a 250 ml reaction vessel equipped with stirrer, thermometer and reflux condenser is placed 100 grams of the compound having the structure:

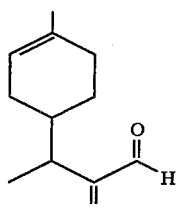

prepared according to Example II, Fraction 4 of U.S. Pat. No. 4,956,481 issued on Sep. 11, 1990. The compound having the structure:

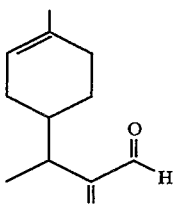

is heated with stirring to a temperature in the range of 182°-190° C. and maintained at that temperature for a period of 5.1 hours. At the end of the reaction, the reaction mass is cooled and fractionally distilled yielding the following fractions:

| Fraction No. | Vapor Temp. (°C.) | Liquid Temp. (°C.) | Vacuum mm/Hg. Pressure |
|---|---|---|---|
| 1 | 33/40 | 78/125 | 95/2.72 |
| 2 | 146 | 157 | 3.10 |
| 3 | 98 | 119 | 2.32 |
| 4 | 106 | 124 | 1.87 |
| 5 | 103 | 200 | 1.69. |

FIG. 2 is the GLC profile for the reaction product. Peaks 20 and 21 of the GLC profile represent product having the structure:

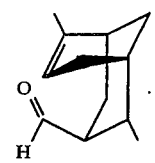

The peak indicated by reference numeral 22 is the peak for the compound having the structure:

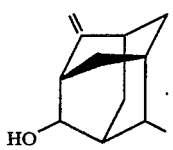

Fraction 4 contains substantially pure product having the structure:

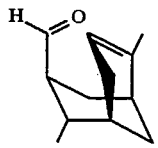

which is a mixture of the isomers having the structures:

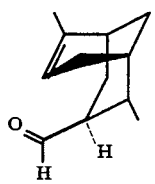

and

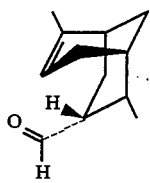

FIG. 3 is the NMR spectrum for the mixture of isomers having the structures:

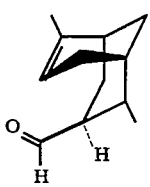

and

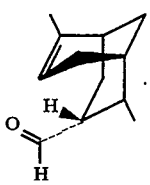

The mixture of isomers having the structures:

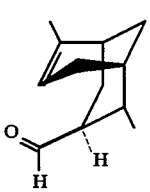

and

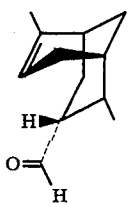

has an earthy and camphoraceous aroma with rooty and vetivert topnotes.

FIG. 4 is the infrared spectrum for the mixture of isomers having the structures:

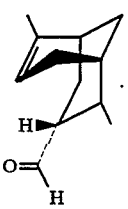

and

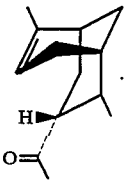

EXAMPLE II

PREPARATION OF 2,6-DIMETHYLBICYCLO[3,3,1]NON-6-ENYL ACRYLONITRILE AND 2,6-DIMETHYLBICYCLO[3,3,1]NON-6-ENYLIDENE PROPIONITRILE

Reactions:

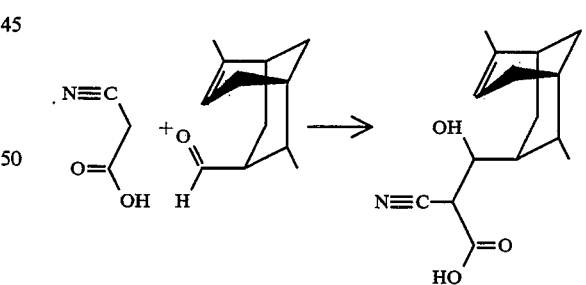

and

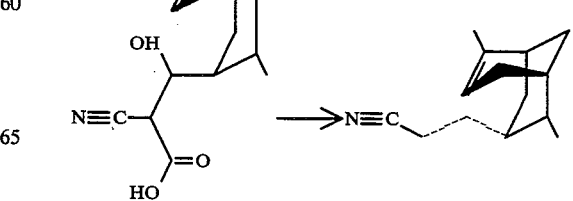

wherein in the mixture of compounds having the structures:

one of the dashed lines represents a carbon-carbon double bond and the other of the dashed lines represents a carbon-carbon single bond.

Into a 5 liter reaction vessel equipped with stirrer, thermometer, reflux condenser, addition funnel and Dean-Stark trap are placed 842 grams of the compound having the structure:

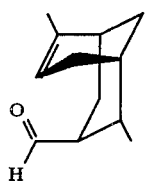

prepared according to Example I (3.88 moles); 396 grams of the compound having the structure:

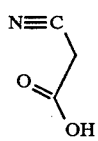

(4.66 moles); 99 grams of ammonium acetate (1.29 moles); and 858 ml toluene.

The reaction mass is heated to reflux (102° C.) and maintained at reflux for a period of 5.5 hours during which time 64 ml of water is evolved and removed via the Dean-Stark trap. The reaction mass is then cooled to room temperature and maintained at room temperature for a period of 20 hours. At the end of the 20 hour period, the reaction mass is then admixed with an additional 800 ml of toluene and heated to reflux at 101° C. and maintained at reflux for a period of 4.5 hours. The reaction mass is then cooled and distilled in a fractional distillation Column yielding the following fractions:

| Fraction No. | Vapor Temp. (°C.) | Liquid Temp. (°C.) | Vacuum mm/Hg. Pressure |
| --- | --- | --- | --- |
| 1 | /90 | /130 | 2:30 |
| 2 | 94 | 135 | 1:87 |
| 3 | 95 | 136 | 1:82 |
| 4 | 96 | 135 | 1:78 |
| 5 | 100 | 139 | 1:75 |
| 6 | 109 | 141 | 1:72 |
| 7 | 115 | 142 | 1:70 |
| 8 | 122 | 143 | 1:83 |
| 9 | 130 | 143 | 2:37 |
| 10 | 126 | 143 | 1:85 |
| 11 | 130 | 143 | 2:11 |
| 12 | 130 | 143 | 1:88 |
| 13 | 135 | 148 | 2:56 |
| 14 | 135 | 148 | 2:50 |
| 15 | 125 | 144 | 1:81 |
| 16 | 125 | 144 | 1:75 |
| 17 | 123 | 143 | 1:56 |
| 18 | 119 | 145 | 1:30 |
| 19 | 117 | 145 | 1:23 |
| 20 | 117 | 145 | 1:19 |
| 21 | 117 | 145 | 1:17 |
| 22 | 118 | 148 | 1:22 |
| 23 | 116 | 148 | 1:09 |
| 24 | 116 | 148 | 1:06 |
| 25 | 126 | 158 | 2:64 |
| 26 | 126 | 155 | 1.68 |
| 27 | 128 | 165 | 2.08 |
| 28 | 134 | 170 | 2:48. |

Bulked distillation Fractions 16-27 have a woody, green, mimosa and violet leaf aroma with green, fruity, woody, violet leaf and mimosa topnotes. Bulked distillation Fractions 16-27 is a mixture of isomers defined according to the structure:

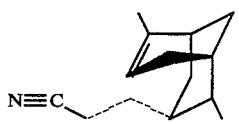

wherein in the mixture in each of the compounds one of the dashed lines is a carbon-carbon double bond and the other of the dashed lines is a carbon-carbon single bond. The mixture of the compounds is actually a mixture of isomers having the structures:

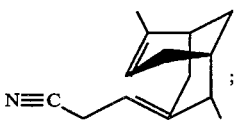
;

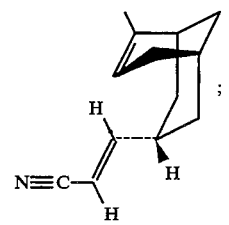
;

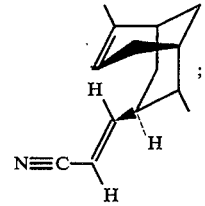
;

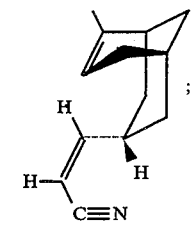

and

-continued

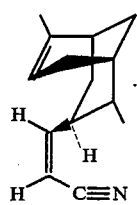

FIG. 5 is the GLC profile for the reaction product of this example. The peaks indicated by reference numerals 50 and 51 are peaks for the mixture of compounds defined according to the structure:

The peak indicated by reference numeral 52 is the peak for the toluene solvent which is distilled in the initial distillation Fractions 1-9.

FIG. 6 is the NMR spectrum for the mixture of compounds having the structure:

FIG. 7 is the infrared spectrum for the mixture of compounds defined according to the structure:

EXAMPLE III

COMPARISON OF PERFUME COMPOSITIONS CONTAINING SUBSTITUTED 2,6-DIMETHYLBICYCLO[3,3,1]NON-6-ENES

A rose perfume is prepared containing the following mixtures:

| Ingredients | Parts by Weight | | |
|---|---|---|---|
| | Example (III-A) | Example (III-B) | Example (III-C) |
| Phodinol | 250 | 250 | 250 |
| Phenylethyl alcohol | 195 | 195 | 195 |
| Alpha methyl ionone | 80 | 80 | 80 |
| Linalyl acetate | 60 | 60 | 60 |
| Cis-3-hexenyl acetate | 5 | 5 | 5 |
| Jasmine absolute | 10 | 10 | 10 |
| Cinnamic alcohol | 20 | 20 | 20 |
| Rhodinyl acetate | 60 | 60 | 60 |
| Cyclohexyl ethyl alcohol | 20 | 20 | 20 |
| Geraniol | 130 | 130 | 130 |
| Geranyl acetate | 80 | 80 | 80 |
| Paraisopropyl cyclohexanol | 60 | 60 | 60 |
| Diethyl phthalate | 30 | 30 | 30 |
| Trans, trans-delta-damascone | 30 | 30 | 30 |
| Mixture of compounds having the structure:  prepared according to Example I, distillation Fraction 4. | 30 | 0 | 0 |
| Mixture of compounds defined according to the structure: 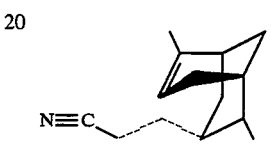 prepared according to Example II, bulked distillation Fractions 16-27. | 0 | 30 | 0 |
| 50:50 Weight:weight mixture of compounds having the structures: 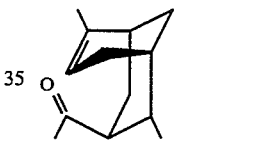 and 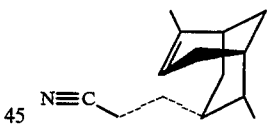 prepared according to Examples I and II, respectively, supra. | 0 | 0 | 30 |

The mixture of isomers having the structure:

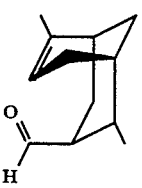

imparts to this rose formulation excellent and substantive earthy and camphoraceous undertones and rooty and vetivert topnotes. Accordingly, the formulation of Example III(A) can be described as "a rosey aroma with earthy and camphoraceous undertones and rooty and vetivert topnotes".

The mixtures of compounds defined according to the structure:

prepared according to Example II bulked distillation Fractions 16–27 imparts to this rosey formulation woody, green, mimosa and violet leaf undertones and green, fruity, woody, violet leaf and mimosa topnotes. Accordingly, the perfume composition of Example III-B can be described as "a rosey aroma having woody, green, mimosa and violet leaf undertones and green, fruity, woody, violet leaf and mimosa topnotes".

The mixture of compounds having the structures:

and

imparts to this rosey formulation earthy, camphoraceous, woody, green, mimosa and violet leaf undertones and rooty, vetivert, green, fruity, woody, violet leaf and mimosa topnotes. Accordingly, the perfume composition of Example III-C can be described as "rosey with earthy, camphoraceous, woody, green, mimosa and violet leaf undertones and rooty, vetivert, green, fruity, woody, violet leaf and mimosa topnotes".

EXAMPLE IV

PREPARATION OF COSMETIC POWDER COMPOSITIONS

Cosmetic powder compositions are prepared by mixing in a ball mill 100 grams of talcum powder with 0.25 grams of each of the substances set forth in Table II below. Each of the cosmetic powder compositions has an excellent aroma as described in Table II below:

TABLE II

| Substance | Aroma Description |
|---|---|
| Mixture of isomers having the structure: 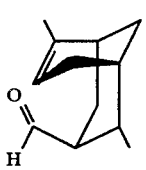 prepared according to Example I, Fraction 4. | An earthy and comphoraceous aroma with rooty and vetivert topnotes. |
| Mixture of isomers having the structure: [structure] prepared according to Example II, bulked distillation Fractions 16–27, wherein in the mixture in each of the compounds one of the dashed lines represents a carbon-carbon double bond and the other of the dashed lines represents a carbon-carbon single bond. | A woody, green, mimosa and violet leaf aroma with green, fruity, woody, violet leaf and mimosa topnotes. |
| Perfume composition of Example III-A. | A rosey aroma with earthy and and- comphoraceous undertones and rooty and vetivert topnotes. |
| Perfume composition of Example III-B. | A rosey aroma having woody, green, mimosa dn violet leaf undertones and green, fruity, woody, violet leaf and mimosa topnotes. |
| Perfume composition of Example III-C. | Rosey with earthy, comphoraceous, woody, green, mimosa and violet leaf undertones and rooty, vetivert, green, fruity, woody, violet leaf and mimosa topnotes. |

EXAMPLE V

PERFUMED LIQUID DETERGENTS

Concentrated liquid detergents (lysine salt of n-dodecylbenzene sulfonic acid as more specifically described in U.S. Pat. No. 3,948,818 issued on Apr. 6, 1976 incorporated by reference herein) with aroma nuances as set forth in Table II of Example IV, are prepared containing 0.10%, 0.15%, 0.20%, 0.25% 0.30% and 0.35% of the substance set forth in Table II of Example IV. They are prepared by adding and homogeneously mixing the appropriate quantity of substance set forth in Table II of Example IV in the liquid detergent. The detergents all possess excellent aromas as set forth in Table II of Example IV, the intensity increasing with greater concentrations of substance as set forth in Table II of Example IV.

EXAMPLE VI

PREPARATION OF COLOGNES AND HANDKERCHIEF PERFUMES

Compositions as set forth in Table II of Example IV are incorporated into colognes at concentrations of 2.0%, 2.5%, 3.0%, 3.5%, 4.0%, 4.5% and 5.0% in 80%, 85%, 90% and 95% aqueous food grade ethanol solutions; and into handkerchief perfumes at concentrations of 15%, 20% 25% and 30% (in 80%, 85%, 90% and 95% aqueous food grade ethanol solutions) Distinctive and definite fragrances as set forth in Table II of Example IV are imparted to the colognes and to the handkerchief perfumes at all levels indicated.

EXAMPLE VII

PREPARATION OF SOAP COMPOSITIONS

One hundred grams of soap chips (per sample) (IVORY ® produced by the Procter & Gamble Company of Cincinnati, Ohio), are each mixed with one gram samples of substances as set forth in Table II of Example IV until homogeneous compositions are obtained. In each of the cases, the homogeneous compositions are heated under 8 atmospheres pressure at 180° C. for a period of three hours and the resulting liquids are placed into soap molds. The resulting soap cakes, on cooling, manifest aromas as set forth in Table I I of Example IV.

EXAMPLE VIII

PREPARATION OF SOLID DETERGENT COMPOSITIONS

Detergents are prepared using the following ingredients according to Example I of Canadian Patent No. 1,007,948 (incorporated by reference herein):

| Ingredient | Percent by Weight |
|---|---|
| NEODOL ® 45-11 (a $C_{14}$-$C_{15}$ alcohol ethoxylated with 11 moles of ethylene oxide) | 12 |
| Sodium carbonate | 55 |
| Sodium citrate | 20 |
| Sodium sulfate, water brighteners | q.s. |

This detergent is a phosphate-free detergent. Samples of 100 grams each of this detergent are admixed with 0.10, 0.15, 0.20 and 0.25 grams of each of the substances as set forth in Table II of Example IV. Each of the detergent samples has an excellent aroma as indicated in Table II of Example IV.

EXAMPLE IX

Utilizing the procedure of Example I at column 15 of U.S. Pat. No. 3,632,396 (the disclosure of which is incorporated herein by reference), non-woven cloth substrates useful as drier-added fabric softening articles of manufacture are prepared wherein the substrate, the substrate coating, the outer coating and the perfuming material are as follows:

1. A water "dissolvable" paper ("Dissolvo Paper");
   ADOGEN ®448 (m.p. about 140° F.) as the substrate coating; and
   An outer coating having the following formulation (m.p. about 150° F.):
   57% $C_{20-22}$HAPS
   22% isopropyl alcohol
   20% antistatic agent
   1% of one of the substances as set forth in Table II of Example IV.

Fabric softening compositions prepared according to Example I at column 15 of U.S. Pat. No. 3,632,396 having aroma characteristics as set forth in Table II of Example IV, supra, consist of a substrate coating having a weight of about 3 grams per 100 square inches of substrate; a first coating located directly on the substrate coating consisting of about 1.85 grams per 100 square inches of substrate; and an outer coating coated on the first coating consisting of about 1.4 grams per 100 square inches of substrate. One of the substances of Table II of Example IV is admixed in each case with the outer coating mixture, thereby providing a total aromatized outer coating weight ratio to substrate of about 0.5:1 by weight of the substrate. The aroma characteristics are imparted in a pleasant manner to the head space in a drier on operation thereof in each case using said drier-added fabric softener non-woven fabrics and these aroma characteristics are described in Table II of Example IV, supra.

EXAMPLE X

HAIR SPRAY FORMULATIONS

The following hair spray formulation is prepared by first dissolving PVP/VA E-735 copolymer manufactured by the GAF Corporation of 140 West 51st Street, New York, N.Y. in 91.62 grams of 95% food grade ethanol. 8.0 Grams of the polymer is dissolved in the alcohol. The following ingredients are added to the PVP/VA alcoholic solution:

| | |
|---|---|
| Dioctyl sebacate | 0.05 weight percent |
| Benzyl alcohol | 0.10 weight percent |
| Dow Corning 473 fluid (prepared by the Dow Corning Corporation) | 0..10 weight percent |
| TWEEN ® 20 surfactant (prepared by ICI America Corporation) | 0.03 weight percent |
| One of the perfumery substances as set forth in Table II of Example IV | 0.10 weight percent |

The perfuming substances as set forth in Table II of Example IV add aroma characteristics as set forth in Table II of Example IV which are rather intense and aesthetically pleasing to the users of the soft-feel, good-hold pump hair sprays.

EXAMPLE XI

CONDITIONING SHAMPOOS

Monamid CMA (prepared by the Mona Industries Company) (3.0 weight percent) is melted with 2.0 weight percent coconut fatty acid (prepared by Procter & Gamble Company of Cincinnati, Ohio); 2.0 weight percent ethylene glycol distearate (prepared by the Armak Corporation) and triethanolamine (a product of Union Carbide Corporation)(1.4 weight percent). The resulting melt is admixed with Stepanol WAT produced by the Stepan Chemical Company (35.0 weight percent). The resulting mixture is heated to 60° C. and mixed until a clear solution is obtained (at 60° C.). This material is "Composition A".

GAFQUAT ®755 N polymer (manufactured by GAF Corporation of 140 West 51st Street, New York, N.Y.)(5.0 weight percent) is admixed with 0.1 weight percent sodium sulfite and 1.4 weight percent polyethylene glycol 6000 distearate produced by Armak Corporation. This material is "Composition B".

The resulting "Composition A" and "Composition B" are then mixed in a 50:50 weight ratio of A:B and cooled to 45° C. and 0.3 weight percent of perfuming substance as set forth in Table II of Example IV is added to the mixture. The resulting mixture is cooled to 40° C. and blending is carried out for an additional one hour in each case. At the end of this blending period, the resulting material has a pleasant fragrance as indicated in Table II of Example IV.

EXAMPLE XII

Scented polyethylene pellets having a pronounced scent as set forth in Table II of Example IV are prepared as follows:

75 Pounds of polyethylene of a melting point of about 220° F. are heated to about 230° F. in a container of the kind illustrated in FIGS. 8 and 9. 25 Pounds of each of the perfume materials of Table II of Example IV, supra, are then added quickly to the liquified polyethylene.

The lid 228 is put in place and the agitating means 273 are actuated. The temperature is maintained at about 225° F. and the mixing is then continued for about 5–15 minutes. The valve "V" is then opened to allow flow of the molten polyethylene enriched with each of the aroma substance-containing materials to exit through the orifices 234. The liquid falling through the orifices 234 solidify almost instantaneously upon impact with the moving, cooled conveyor 238. Solid polyethylene beads or pellets 244 having pronounced aromas as set forth in Table II of Example IV, supra, are then formed. Analysis demonstrates that the pellets contain about 25% of each of the perfume substances of Table II of Example IV so that alsmost no losses of the scenting substance occur. These pellets may be called master pellets.

50 Pounds of the scent-containing master pellets are then added to 1,000 pounds of unscented polyethylene powder and the mass is heated to the liquid state. The liquid is molded into thin sheets or films. The sheets or films have a pronounced aroma as set forth in Table II of Example IV, supra. The sheets are also fabricated into garbage bags which have aromas as set forth in Table II of Example IV, supra.

What is claimed is:

1. A substituted 2,6-dimethylbicyclo[3,3,1]non-6-ene derivative defined according to the structure:

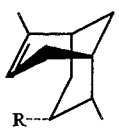

wherein R is a moiety selected from the group consisting of:

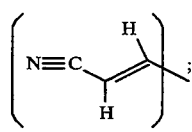

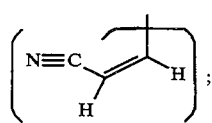

and

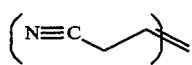

wherein the dashed line represents a carbon-carbon single bond or a carbon-carbon double bond.

2. The 2,6-dimethylbicyclo[3,3,1]non-6-ene derivative of claim 1 having a structure selected from the group consisting of:

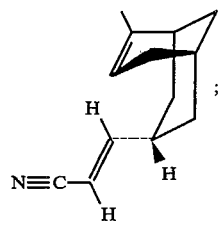

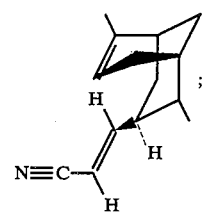

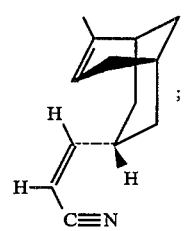

and

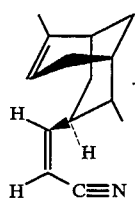

3. A mixture of 2,6-dimethylbicyclo[3,3,1]non-6-ene derivatives of claim 1 defined according to the structure:

wherein, in the mixture one of the dashed lines represents a carbon-carbon single bond and the other of the dashed lines represents a carbon-carbon double bond.

4. A 2,6-dimethylbicyclo[3,3,1]non-6-ene derivative defined according to the structure:

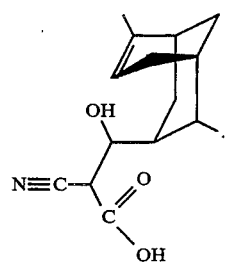

5. A process for augmenting or enhancing the aroma of a consumable material selected from the group consisting of perfume compositions, perfumed articles and colognes comprising the step of intimately admixing with a perfume base, a perfumed article base or a cologne base an aroma augmenting, enhancing or imparting quantity of at least one compound defined according to claim 1.

6. A process for augmenting or enhancing the aroma of a consumable material selected from the group consisting of perfume compositions, perfumed articles and colognes comprising the step of intimately admixing with a perfume base, a perfumed article base or a cologne base an aroma augmenting, enhancing or imparting quantity of at least one compound defined according to claim 2.

7. A process for augmenting, enhancing or imparting an aroma in or to a perfume composition, a perfumed article or a cologne comprising the step of intimately admixing with said perfume composition, cologne or perfumed article an aroma imparting, augmenting or enhancing quantity of the composition defined according to claim 3.

8. A perfume composition comprising a perfume base and intimately admixed therewith an aroma augmenting, enhancing or imparting quantity of a composition defined according to claim 1.

9. A perfumed article comprising a perfumed article base and intimately admixed therewith an aroma augmenting, enhancing or imparting quantity of a composition of matter defined according to claim 1.

10. A cologne consisting essentially of water, ethanol and an aroma imparting quantity of a composition of matter defined according to claim 1.

11. A perfume composition comprising a perfume base and intimately admixed therewith an aroma imparting, augmenting or enhancing quantity of the composition of matter defined according to claim 3.

12. A perfumed article comprising a perfumed article base and intimately admixed therewith an aroma augmenting, enhancing or imparting quantity of the composition of matter defined according to claim 3.

13. A cologne comprising water, ethanol and an aroma imparting quantity of the composition of matter defined according to claim 3.

14. A perfumed polymer comprising a microporous polymer and intimately admixed therewith and contained in the interstices thereof an aroma imparting quantity of a composition of matter defined according to claim 1.

15. A perfumed polymer comprising a microporous polymer and intimately admixed therewith and contained in the interstices thereof an aroma imparting quantity of a composition of matter defined according to claim 2.

16. A perfumed polymer comprising a microporous polymer and intimately admixed therewith and contained in the interstices thereof an aroma imparting quantity of a composition of matter defined according to claim 3.

17. A process for augmenting the aroma of a consumable material selected from the group consisting of perfume compositions, perfumed articles and colognes comprising the step of intimately admixing with a perfume base, a perfumed article base or a cologne base an aroma augmenting, enhancing or imparting quantity of the 2,6-dimethylbicyclo[3,3,1]non-6-ene derivative having the structure:

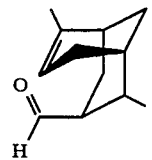

in substantially pure form.

18. A perfume composition comprising a perfume base and intimately admixed therewith an aroma augmenting, enhancing or imparting quantity of the 2,6-dimethylbicyclo[3,3,1]non-6-ene derivative having the structure:

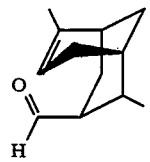

in substantially pure form.

19. A perfumed article comprising a perfume base and intimately admixed therewith an aroma augmenting, enhancing or imparting quantity of the 2,6-dimethylbicyclo[3,3,1]non-6-ene derivative having the structure:

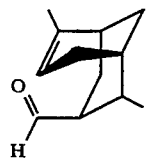

in substantially pure form.

20. A cologne consisting essentially of water, ethanol and an aroma imparting quantity of the 2,6-dimethylbicyclo[3,3,1]non-6-ene derivative having the structure:

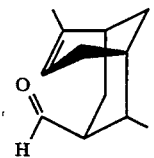

in substantially pure form.

21. A perfumed polymer comprising a microporous polymer and intimately admixed therewith and contained in the interstices thereof an aroma imparting quantity of the 2,6-dimethylbicyclo[3,3,1]non-6-ene derivative having the structure:

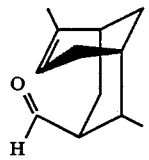

in substantially pure form.

* * * * *